(12) United States Patent
Chenard et al.

(10) Patent No.: US 6,921,764 B2
(45) Date of Patent: Jul. 26, 2005

(54) THIENO-PYRIMIDIN-4-ONE AMPA ANTAGONISTS

(75) Inventors: Bertrand L Chenard, Waterford, CT (US); Willard M Welch, Mystic, CT (US); Anthony R. Reinhold, Mystic, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/640,482

(22) Filed: Aug. 13, 2003

(65) Prior Publication Data

US 2004/0049039 A1 Mar. 11, 2004

Related U.S. Application Data

(62) Division of application No. 09/079,420, filed on May 14, 1998, now Pat. No. 6,627,755.
(60) Provisional application No. 60/049,082, filed on Jun. 9, 1997, provisional application No. 60/050,110, filed on Jun. 13, 1997, and provisional application No. 60/053,274, filed on Jul. 21, 1997.

(51) Int. Cl.[7] ..................... C07D 495/04; A61K 31/519
(52) U.S. Cl. ..................................... 514/260.1; 544/278
(58) Field of Search ....................... 544/278; 514/260.1

(56) References Cited

U.S. PATENT DOCUMENTS

| 5,284,957 A | 2/1994 | Huff ............................ 548/112 |
| 5,426,106 A | 6/1995 | Kulagowski et al. ..... 514/233.2 |
| 6,136,812 A | * 10/2000 | Chenard et al. .......... 514/266.2 |

FOREIGN PATENT DOCUMENTS

| EP | 0459561 | 12/1991 |
| EP | 0481676 | 4/1992 |
| WO | WO 9311115 | 6/1993 |
| WO | WO 9519346 | 7/1995 |

OTHER PUBLICATIONS

Rogawski et al., PubMed Abstract (Adv Neurol 79:947–63), 1999.*
Liu et al., PubMed Abstract (Proc Natl Sci USA, 101(9):3172–7), Mar. 2004.*
Broadbent et al., PubMed Abstract (Psychopharmacology (Berl). 167(3):225–34), Apr. 2003.*
Sang et al., Abstract #S27.002, May 2001.*
Damasio, Alzheimer's Disease and Related Dementias, Cecil Textbook of Medicine, 20th Edition, vol. 2, pp. 1992–1996, 1996.*
Watkins, J.C, and Evans, R.H., Excitatory Amino Acid Transmitters, Annu. Rev. Pharmacol. Toxicol. 21, pp. 165–204 (1981).
Monaghan, Daniel T., et al., The Excitatory Amimo Acid Receptors: Their Classes, Pharmacology, and Distinct Properties in the Function of the Central Nervous System, Annu. Rev. Parmacol. Toxicol. 29 pp. 365–402 (1989).
Watkins, Jeff C., et al., Structure–activity relationships in the development of excitatory amino acid receptor agonists and competitive antagonists, TIPS– (vol. 11) pp. 25–33 Jan. 1990.
Schoepp, Darryle, et al., Pharmacological and functional characteristics of metabotropic excitatory amino acid receptors, TIPS– (vol. 11) pp. 508–515 Dec. 1990.
McDonald, John W. and Johnston, Michael V., Physiological and pathophysiological roles of excitatory amino acids during central nervous system development, Brain Res. Reviews 15, pp. 41–70 (1990).
Sheardown, Malcom J., et al., 2,3–Dihydroxy–6–nitro–7–sulfamoyl–benzo(F) quinoxaline: A Neuroprotectant for Cerebral Ischemia, Science Reports, vol. 247, pp. 571–574 Feb. 2, 1990.
Buchan, Alastair M., et al., Delayed AMPA receptor blockade reduces cerebral infarction induced by focal ischemia, NeuroReport 2, No. 8, pp. 473–476 (1991).
Le Peillet, Elaine, et al., The non–NMDA antagonists, NBQX and GYKI 52466, protect against cortical and striatal cell loss following transient global ischaemia in the rat, Brain Res. 571, pp. 115–120 (1992).
Parks T.N., et al., Modulation of N–methyl–D–aspartate receptor–mediated increases in cytosolic calcium in cultured rat cerebellar granule cells, Brain Res. 552, pp. 13–22 (1991).
Physicians' Desk Reference, 53 Ed., 1999, pp. 2604–2607.
Meldrum, B.S. Current Opinion in Neurology and Neurosurgery, vol. 5, 1992, pp. 508–513.
Keppelle, L.J. et al. Pharmaceutisch Weekblad, vol. 132 No. 31, 1997, pp. 1117–1123.
Jackson, C.E. et al. Seminars in Neurology, vol. 18, No. 1, 1998, pp. 27–39.
Hughes, A.J. Drugs, vol. 53, No. 2, 1997, pp. 195–205.
Greenamyre, J.T. Neurobiology of Aging, 1989, vol. 10, pp. 593–602.
Medline abstract no. 92274400: Giuffra, M.E. et al. Clinical Neuropharmacology, 1992, vol. 15, No. 2, pp. 148–151.
Medline abstract no. 97339045: Montastruc, J.L. et al. Neuroscience and Biobehavioural Reviews, 1997, vol. 21, No. 4, pp. 477–480.
Chalmers et al. TIPS, 1996, vol. 17, pp. 166–172.
Frampton et al. Drugs and Aging, 1995, vol. 7, No. 6, pp. 480–503.
Lyrer Schweiz. Med. Wochenschr. 1994, vol. 124, No. 45, pp. 2005–2012.

* cited by examiner

*Primary Examiner*—Deepak Rao
(74) *Attorney, Agent, or Firm*—Peter C. Richardson; Lorraine B. Ling; James A. Jubinsky

(57) ABSTRACT

The present invention relates to novel quinazolin-4-one derivatives of the formula I, as defined in the specification, pharmaceutical compositions containing such compounds the use of such compounds to treat neurodegenerative, psychotropic, and drug and alcohol induced central and peripheral nervous system disorders.

15 Claims, No Drawings

THIENO-PYRIMIDIN-4-ONE AMPA ANTAGONISTS

This is a Divisional Application of Parent U.S. Ser. No. 09/079,420 filed May 14, 1998 now U.S. Pat. No. 6,627,755, and claims benefit to same under 35 USC § 120, said parent in turn claiming benefit under 35 USC 119 (e) of U.S. Provisional Application Nos: 60/049,082 filed Jun. 9, 1997; 60/050,110 filed Jun. 13, 1997; and 60/053,274 filed Jul. 21, 1997.

BACKGROUND OF THE INVENTION

The present invention relates to quinazolin-4-ones of the formula I, as described below, their pharmaceutically acceptable salts, pharmaceutical compositions containing them and their use in treating neurodegenerative, psychotropic, and drug and alcohol induced central and peripheral nervous system disorders.

The role of excitatory amino acids, such as glutamic acid and aspartic acid, as the predominant mediators of excitatory synaptic transmission in the central nervous system has been well established. Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). These amino acids function in synaptic transmission primarily through excitatory amino acid receptors. These amino acids also participate in a variety of other physiological processes such as motor control, respiration, cardiovascular regulation, sensory perception, and cognition.

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective agonists N-methyl-D-aspartate (NMDA), α-amino-3-hydroxy-5-methylisoxazole-4-propionic acid (AMPA), and kainic acid (KA). The second general type is the G-protein or second messenger-linked "metabotropic" excitatory amino acid receptor. This second type, when activated by the agonists quisqualate, ibotenate, or trans-1-aminocyclopentane-1,3-dicarboxylic acid, leads to enhanced phosphoinositide hydrolysis in the postsynaptic cell. Both types of receptors appear not only to mediate normal synaptic transmission along excitatory pathways, but also participate in the modification of synaptic connection during development and changes in the efficiency of synaptic transmission throughout life. Schoepp, Bockaert, and Sladeczek. *Trends in Pharmacol. Sci.*, 11, 508 (1990); McDonald and Johnson, *Brain Research Reviews*, 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

Excitatory amino acid excitotoxicity has been implicated in the pathophysiology of a number of neurological disorders. This excitotoxicity has been implicated in the pathophysiology of acute and chronic neurodegenerative conditions including stroke, cerebral ischemia, spinal cord trauma, head trauma, Alzheimer's Disease, Huntington's Chorea, amyotrophic lateral sclerosis, epilepsy, AIDS-induced dementia, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, ocular damage and retinopathy, idiopathic and drug-induced Parkinson's Disease and cerebral deficits subsequent to cardiac bypass surgery and grafting. Other neurological conditions, that are caused by glutamate dysfunction, require neuromodulation. These other neurological conditions include muscular spasms, migraine headaches, urinary incontinence, psychosis, addiction withdrawal (such as alcoholism and drug addiction including opiate, cocaine and nicotine addiction), opiate tolerance, anxiety, emesis, brain edema, chronic and acute pain, convulsions, retinal neuropathy, tinnitus and tardive dyskinesia. The use of a neuro-protective agent, such as an AMPA receptor antagonist, is believed to be useful in treating these disorders and/or reducing the amount of neurological damage associated with these disorders. The excitatory amino acid receptor (EAA) antagonists are also useful as analgesic agents.

Several studies have shown that AMPA receptor antagonists are neuroprotective in focal and global ischemia models. The competitive AMPA receptor antagonist NBQX (2,3-dihydroxy-6-nitro-7-sulfamoylbenzo[f-]quinoxaline) has been reported effective in preventing global and focal ischemic damage. Sheardown et al., *Science*, 247, 571 (1900); Buchan et al., *Neuroreport*, 2, 473 (1991); LePeillet et al., *Brain Research*, 571, 115(1992). The noncompetitive AMPA receptor antagonist GKYI 52466 has been shown to be an effective neuroprotective agent in rat global ischemia models. LaPeillet et al., *Brain Research*, 571, 115 (1992). These studies strongly suggest that the delayed neuronal degeneration in brain ischemia involves glutamate excitotoxicity mediated at least in part by AMPA receptor activation. Thus, AMPA receptor antagonists may prove useful as neuroprotective agents and improve the neurological outcome of cerebral ischemia in humans.

SUMMARY OF THE INVENTION

The present invention relates to compounds of the formula

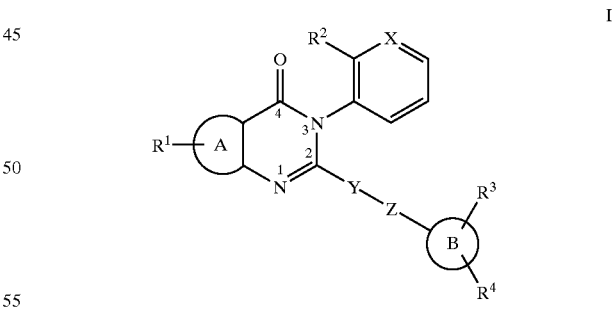

wherein A is a benzo or thieno fused aromatic ring;
B is phenyl, pyridyl or pyrimidyl;
X is N or CH;
Y and Z, taken together, i.e., Y-Z, are either —CH$_2$NH— or —NHCH$_2$—;
R$^1$ is selected from hydrogen, (C$_1$–C$_5$)alkyl optionally substituted with from one to three fluorine atoms, cyano, halo, amino, nitro and (C$_1$–C$_6$)alkoxy optionally substituted with from one to three fluorine atoms;
R$^2$ is halo, cyano, (C$_1$–C$_6$) alkyl optionally substituted with from one to three fluorine atoms, nitro, amino, (C$_1$–C$_6$)

alkylthio, $(C_1-C_6)$alkoxy optionally substituted with from one to three fluorine atoms, hydroxy, H—C(=O)—, $(C_1-C_6)$alkyl-O—C(=O)— or $NH_2$—C(=O)—;

$R^3$ and $R^4$ are selected, independently, from hydrogen, $(C_1-C_6)$alkyl optionally substituted with from one to three fluorine atoms, halo, cyano, hydroxy $(C_1-C_6)$alkoxy optionally substituted with from one to three fluorine atoms, —C(=O)H, —$CH_2OR^5$ and —$CH_2NR^6R^7$;

$R^5$ is hydrogen, $(C_1-C_6)$alkyl or —C(=O)$(C_1-C_6)$alkyl; and $R^6$ and $R^7$ are selected, independently, from hydrogen, $(C_1-C_6)$alkyl, —C(=O)H and —C(=O)$(C_1-C_6)$alkyl;

or $R^6$ and $R^7$, taken together with the nitrogen to which they are attached, form a four to seven membered saturated or unsaturated ring wherein one of the carbon atoms of such ring may optionally be replaced by oxygen or nitrogen (for example, a morpholine, piperidine, pyrrolidine, piperizine, azetidine, pyrrole, pyridine or oxazoline ring);

and the pharmaceutically acceptable salts of such compounds.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

Examples of preferred compounds of the formula I are those wherein $R^1$ is fluoro.

Other Examples of preferred compounds of the formula I are those wherein Y-Z is —$CH_2NH$—, ring A is a benzo ring and $R^1$ is fluoro.

Other examples of preferred compounds of the formula I are wherein $R^2$ is halo, methyl or trifluoromethyl.

Other examples of preferred compounds of the formula I are those wherein Y-Z is —$CH_2NH$—, ring A is a benzo ring, $R^1$ is fluoro, ring B is 2-pyridyl or phenyl and $R^3$ is cyano, fluoro, methyl or —$CH_2NR^6R^7$.

Other more specific embodiments of this invention are the following:

(a) compounds of the formula I wherein ring A is benzo;
(b) compounds of the formula I wherein ring A is thieno;
(c) compounds of the formula I wherein ring B is phenyl;
(d) compounds of the formula I wherein ring B is a pyridine or pyrimidine ring; and
(e) compounds of the formula I wherein $R^6$ and $R^7$, together with the nitrogen to which they are attached, form a morpholine or pyrrolidine ring.

Examples of specific compounds of this invention are:

3-(2-chloro-phenyl)-6-fluoro-2-[(pyridin-2-ylmethyl)-amino]-3H-quinazolin-4-one;

5-fluoro-3-(2-methyl-phenyl)-2-[(pyridin-2-ylmethyl)-amino]-3H-quinazolin-4-one;

3-(2-chloro-phenyl)-6-fluoro-2-[(2-fluorophenyl-methyl)-amino]-3H-quinazolin-4-one;

3-(2-chloro-phenyl)-2-[(2-cyanophenyl-methyl)-amino]-6-fluoro-3H-quinazolin-4-one;

3-(2-chloro-phenyl)-2-[(6-diethylaminomethylpyridin-2-ylmethyl)-amino]-6-fluoro-3H-quinazolin-4-one;

3-(2-chloro-phenyl)-6-fluoro-2-[(6-pyrrolidin-1-ylmethyl-pyridin-2-ylmethyl)-amino]-3H-quinazolin-4-one;

3-(2-chloro-phenyl)-2-[(3-pyrrolidin-1-ylmethyl-phenylamino)-methyl]-3H-thieno[3,2-d]pyrimidin-4-one;

3-(2-methyl-phenyl)-2-[(3-pyrrolidin-1-ylmethyl-phenylamino)-methyl]-3H-thieno[3,2-d]pyrimidin-4-one;

3-(2-chloro-phenyl)-2-[(2-fluoro-phenylamino)-methyl]-3H-thieno[3,2-d]pyrimidin-4-one;

3-(2-chloro-pyrid-3-yl)-2-[(3-pyrrolidin-1-ylmethyl-phenylamino)-methyl]-3H-thieno[3,2-]pyrimidin-4-one;

2-{[3-(2-chloro-pyrid-3-yl)-4-oxo-3,4-dihydro-thieno[3,2-d]pyrimidin-2-ylmethyl]-amino}-benzonitrile;

3-(2-chloro-phenyl)-2-[(3-pyrrolidin-1-ylmethyl-phenylamino)-methyl]-3H-quinazolin-4-one;

6-chloro-3-(2-chloro-phenyl)-2-[(3-pyrrolidin-1-ylmethyl-phenylamino)-methyl]-3H-quinazolin-4-one;

6-chloro-3-(2-chloro-phenyl)-2-[(3-diethylaminomethyl-phenylamino)-methyl]-3H-quinazolin-4-one;

6-chloro-3-(2-chloro-pyrid-3-yl)-2-[(3-diethylaminomethyl-phenylamino)-methyl]-3H-quinazolin-4-one;

6-chloro-3-(2-trifluoromethyl-phenyl)-2-[(3-diethylaminomethyl-phenylamino)-methyl]-3H-quinazolin-4-one;

2-{[3-(2-chloro-pyridin-3-yl)-4-oxo-3,4-dihydro-quinazolin-2-ylmethyl]-amino}-benzonitrile;

2-{[3-(2-methyl-pyridin-3-yl)-4-oxo-3,4-dihydro-quinazolin-2-ylmethyl]-amino}-benzonitrile;

2-{[6-fluoro-3-(2-methyl-phenyl)-4-oxo-3,4-dihydro-quinazolin-2-ylmethyl]-amino}-nicotinonitrile; and 2-{[3-(2-chloro-phenyl)-4-oxo-3,4-dihydro-quinazolin-2-ylmethyl]-amino}-nicotinonitrile.

This invention also relates to a pharmaceutical composition for treating a condition selected from stroke, cerebral ischemia, spinal cord trauma, head trauma, Alzheimer's Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), ocular, damage, retinopathy, retinal neuropathy, tinnitus, idiopathic and drug induced Parkinson's Disease, anxiety, emesis, brain edema, chronic or acute pain, tardive dyskinesia and cerebral deficits subsequent to cardiac bypass surgery and grafting, in a mammal, comprising an amount of a compound of formula I that is effective in treating such condition and a pharmaceutically acceptable carrier.

This invention also relates to a method of treating a condition selected from stroke, cerebral ischemia, spinal cord trauma, head trauma, Alzheimer's Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), ocular damage, retinopathy, retinal neuropathy, tinnitus, idiopathic and drug induced Parkinson's Disease, anxiety, emesis, brain edema, chronic or acute pain, tardive dyskinesia and cerebral deficits subsequent to cardiac bypass surgery and grafting, in a mammal, comprising administering to a mammal in need of such treatment an amount of a compound of formula I that is effective in treating such condition.

This invention also relates to a pharmaceutical composition for treating a disorder or condition, the treatment of which can be effected or facilitated by reducing or inhibiting glutamate neurotransmission in a mammal, comprising an amount of a compound of formula I, or a pharmaceutically effective salt thereof, that is effective in treating such disorder or condition and a pharmaceutically acceptable carrier.

This invention also relates to a method of treating a disorder or condition, the treatment or prevention of which can be effected or facilitated by reducing or inhibiting glutamate neurotransmission in a mammal, comprising administering to a mammal in need of such treatment an amount of a compound of formula I, or a pharmaceutically effective salt thereof, that is effective in treating such disorder or condition.

This invention also relates to a pharmaceutical composition for treating a condition selected from stroke, cerebral ischemia, spinal cord trauma, head trauma, Alzheimer's Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), ocular damage, retinopathy, retinal neuropathy, tinnitus, idiopathic and drug induced Parkinson's Disease, anxiety, emesis, brain edema, chronic or acute pain, tardive dyskinesia and cerebral deficits subsequent to cardiac bypass surgery and grafting, in a mammal, comprising an AMPA receptor antagonizing effective amount of a compound of formula I, or a pharmaceutically salt thereof, and a pharmaceutically acceptable carrier.

This invention also relates to a method for treating a condition selected from stroke, cerebral ischemia, spinal cord trauma, head trauma, Alzheimer's Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), ocular damage, retinopathy, retinal neuropathy, tinnitus, idiopathic and drug induced Parkinson's Disease, anxiety, emesis, brain edema, chronic or acute pain, tardive dyskinesia and cerebral deficits subsequent to cardiac bypass surgery and grafting, in a mammal, comprising administering to a mammal requiring such treatment an AMPA receptor antagonizing effective amount of a compound of formula I, or a pharmaceutically acceptable salt thereof.

This invention also relates to a pharmaceutical composition for treating a disorder or condition, the treatment of which can be effected or facilitated by reducing or inhibiting glutamate neurotransmission in a mammal, comprising an AMPA receptor antagonizing effective amount of a compound of formula I, or a pharmaceutically acceptable salt thereof, and a pharmaceutically acceptable carrier.

This invention also relates to a method for treating a disorder or condition, the treatment of which can be effected or facilitated by reducing or inhibiting glutamate neurotransmission in a mammal, comprising administering to a mammal requiring such treatment an AMPA receptor antagonizing effective amount of a compound of formula I or a pharmaceutically acceptable salt thereof.

Unless otherwise indicated, the alkyl groups referred to herein, as well as the alkyl moieties of other groups referred to herein (em, alkoxy), may be linear or branched, and they may also be cyclic (e.g., cyclopropyl, cyclobutyl, cyclopentyl, or cyclohexyl) or be linear or branched and contain cyclic moieties.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

Unless otherwise indicated, "halo" and "halogen", as used herein, refer to fluorine, bromine, chlorine or iodine.

Compounds of the formula I may have chiral centers and therefore may exist in different enantiomeric and diastereomic forms. This invention relates to all optical isomers and all stereoisomers of compounds of the formula I and mixtures thereof, and to all pharmaceutical compositions and methods of treatment defined above that contain or employ them, respectively.

Due to the substituent on the carbon at position "2" and the carbonyl group on the carbon at position "4" of the quinazolin-4-one of formula I, the ring attached to the nitrogen at position "3" can not rotate freely. This restricted rotation means that compounds of the formula I exist in two isomeric forms or atropisomers. These atropisomers can be separated.

This invention includes, for example, those stereoisomers of compounds of the formula I that are atropisomers. Atropisomers are isomeric compounds that are chiral, i.e., each isomer is not superimposable on its mirror image and the isomers, once separated, rotate polarized light in equal but opposite directions. Atropisomers are distinguished from enantiomers in that atropisomers do not possess a single asymmetric atom. Such compounds are conformational isomers which occur when rotation about a single bond in the molecule is prevented or greatly slowed as a result of steric interactions with other parts of the molecule and the substituents at both ends of the single bond are unsymmetrical. A detailed account of atropisomers can be found in Jerry March, *Advanced Organic Chemistry*, 101–102 (4th ed. 1992) and in Oki, *Top. Stereochem.*, 14, 1–81 (1983).

The following structure depicts the atropisomerism of the compound of formula I.

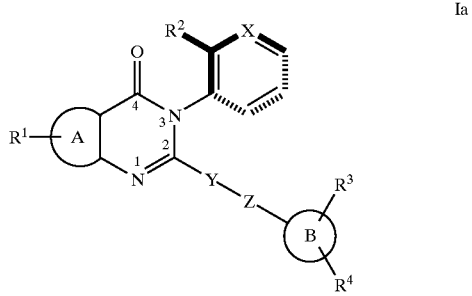

Ia

The bold lines in formula Ia indicate that the bolded atoms, and the groups attached thereto, are sterically restricted so as to exist orthogonally above the plane of the quinazolinone ring. This steric restriction is due to a rotational energy barrier preventing free rotation about the single bond connecting the nitrogen at position "3" of the quinazolinone ring to the X-containing (i.e., phenyl or pyridyl) aryl group.

Formulas I and Ia above include compounds identical to those depicted but for the fact that one or more hydrogen, carbon or other atoms are replaced by isotopes thereof. Such compounds are useful as research and diagnostic tools in metabolism pharmacokinetic studies and in binding assays. Specific applications in research include radioligand binding assays, autoradiography studies and in vivo binding studies.

DETAILED DESCRIPTION OF THE INVENTION
The compounds of formula I can be prepared according to the methods of Scheme 1. In the reaction Scheme and discussion that follow, unless otherwise indicated, rings A and B and substituents $R^1$ through $R^7$, Y and Z are as defined above for formula I.
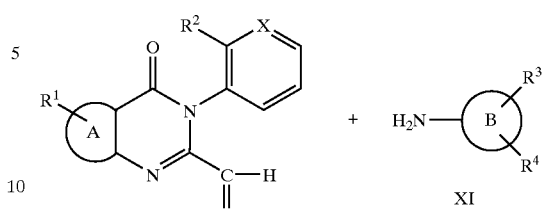
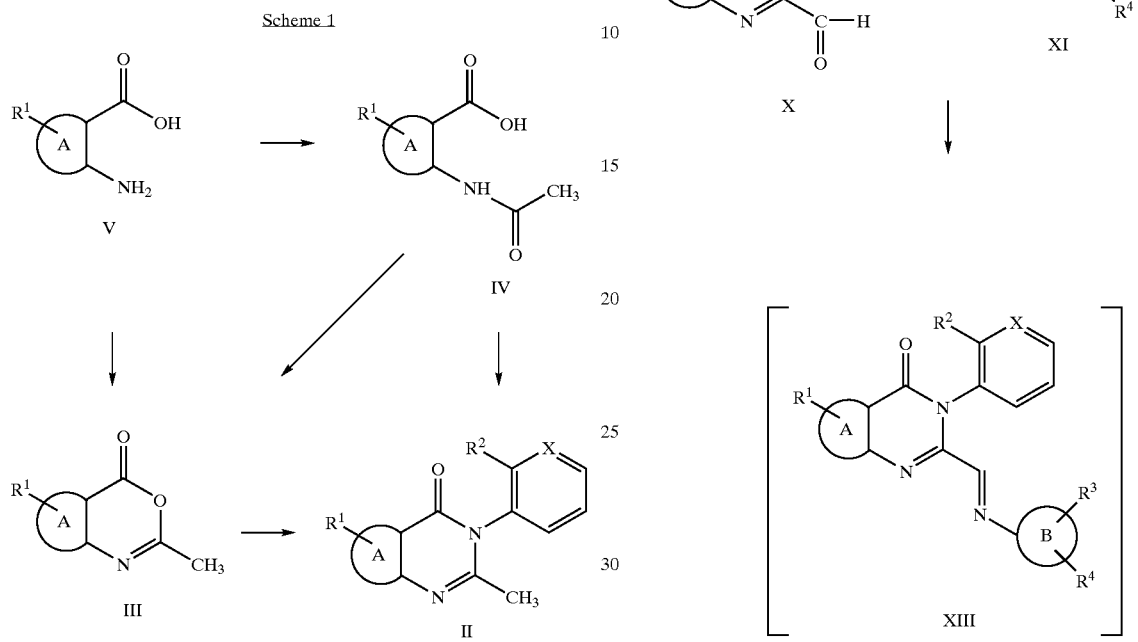
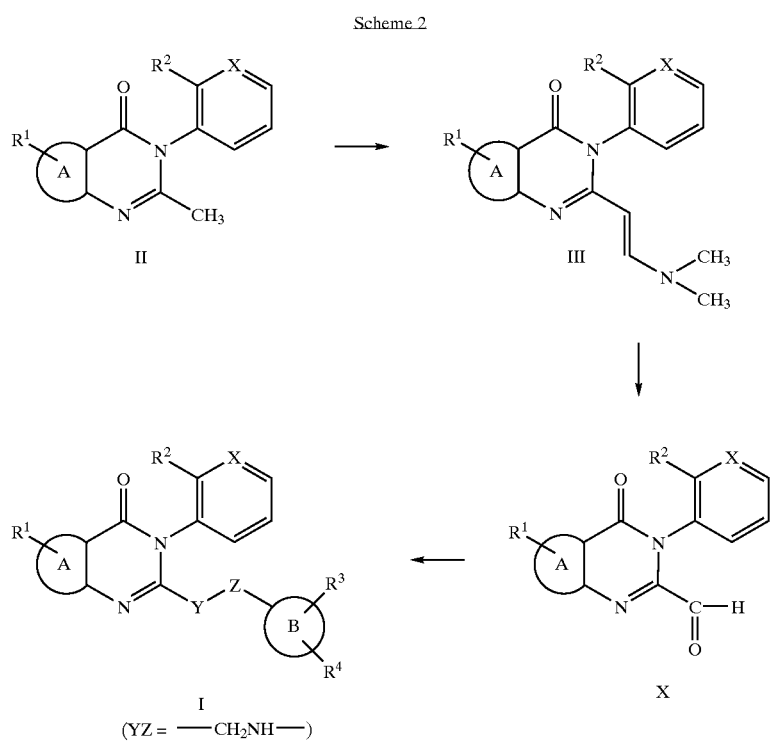

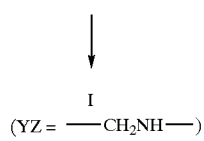

Scheme 4

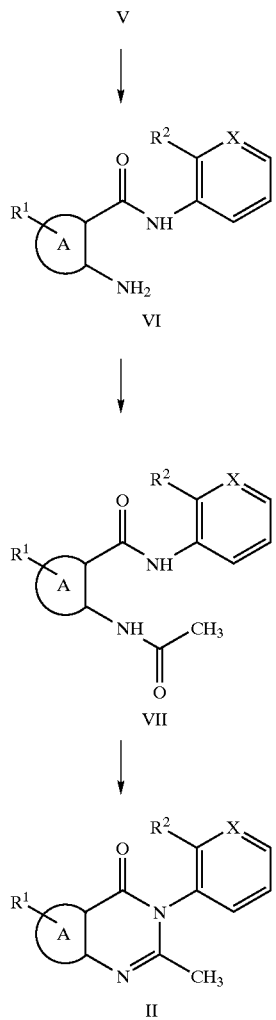

Scheme 5

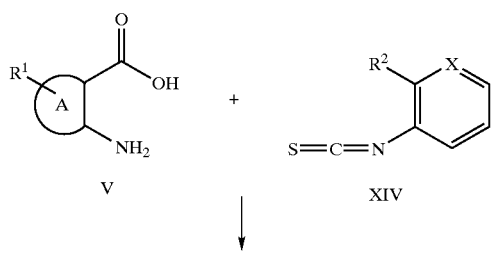

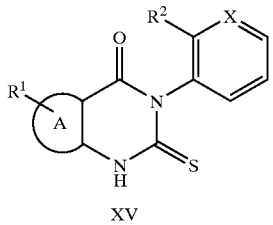

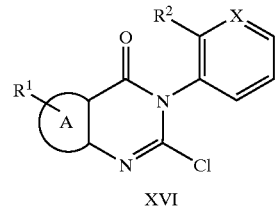

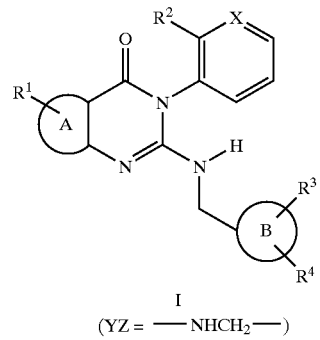

Scheme 1 illustrates methods of preparing intermediates of the formula II, which can then be converted into compounds of the formula I. Referring to Scheme 1, a compound of the formula V can be converted into an acetamide of the formula IV by reactioning it with acetyl chloride or acetic anhydride in the presence of a base in a reaction inert solvent. Suitable solvents include methylene chloride, dimethoxyethane, t-butyl methyl ether, dichloroethane, tetrahydrofuran and dioxane. Suitable bases include trialkylamines such as triethylamine and tributylamine, dimethylaminopyridine and potassium carbonate, preferably triethylamine. The temperature of this reaction is in the range from about 0° C. to about 100° C. for about 1 hour to about 10 hours, preferably at about 0° C. to 30° C. for about 3 hours.

The acetamide of formula IV can be cyclized to form a compound of the formula III by reaction with a dehydrating agent, in the presence of a catalyst, in a dry reaction inert solvent. Suitable dehydrating agents include acetic anhydride, phosphorus pentoxide, dicyclohexylcarbodiimide, and acetyl chloride, preferably acetic anhydride. Suitable catalysts include sodium or potassium acetate, acetic acid, p-toluene sulfonic acid, or boron trifluoride etherate, preferably sodium acetate. Suitable solvents include dioxane, toluene, diglyme or dichloroethane, preferably dioxane. The temperature for this reaction can range from about 0° C. to about 150° C. and the reaction is generally carried out for about 1 hour to about 24 hours. Preferably, the reaction is conducted at about 80° C. to 100° C. for about 3 to 10 hours.

Alternatively, the compound of formula V can be converted directly into a compound of formula III by reacting it with acetic anhydride in the presence of an acid catalyst in a solvent. Examples of acid catalysts that can be used are acetic acid, sulfuric acid and p-toluene sulfonic acid. Acetic acid is preferred. Examples of solvents that can be used are toluene and xylene. Acetic acid is also the preferred solvent. The temperature for this reaction can range from about 20° C. to about 150° C. and the reaction is typically carried at for about 10 minutes to about 10 hours. The reaction is preferably carried out at about 80° C. to 120° C. for about 2 to 5 hours.

The compound of formula III, formed by either of the above methods, can then be reacted with an amine of the formula

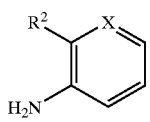

VIII in a polar protic solvent, in the presence of an acid catalyst, to form a compound of the formula II. Suitable acid catalysts include acetic acid, p-toluene sulfonic acid and sulfuric acid, with acetic acid being preferred. Suitable polar protic solvents include acetic acid, methanol, ethanol and isopropanol, with acetic acid being preferred. This reaction is generally carried out at a temperature from about 20° C. to about 150° C. for about 1 hour to about 24 hours, preferably for about 6 hours at about 80° C. to 120° C.

Alternatively, a compound of the formula IV can be directly converted to a compound of the formula II by reaction with a dehydrating agent, an amine of the formula VIII, as described above, and a base, in a reaction inert solvent. Examples of dehydrating agents that can be used are phosphorous trichloride, phosphorous oxychloride, phosphorous pentachloride and thionyl chloride, with phosphorous trichloride being preferred. Suitable bases include pyridine, lutidine, diisopropylethylamine, dimethylaminopyridine, triethylamine and N-methyl morpholine. Suitable solvents include toluene, cyclohexane, benzene and xylene. Preferably, pyridine is used as the base and the reaction is carried at in a toluene solvent. Under some circumstances, when the combined reactants are a liquid, the reaction may be run neat. The temperature can range from about 50° C. to about 150° C., and the reaction is generally allowed to run for about 1 hour to about 24 hours. It is preferably carried out at about 80° C. to 120° C. for about 2–8 hours.

Scheme 2 illustrates the synthesis of compounds of formula I from the corresponding compounds of formula II. Referring to Scheme 2, reaction of a compound of the formula II with dimethylformamide dimethyl acetal complex (DMF·DMA) in dimethylformamide (DMF) at a temperature from about 50° C. to about 180° C., preferably from about 100° C. to about 150° C. yields, the corresponding amines of formula IX.

The aldehydes of formula X can be formed by reacting the corresponding enamines of formula IX with sodium periodate (NaIO$_4$) or potassium permanganate (KMnO$_4$) in a solvent mixture containing water and an organic solvent such as ether, dimethoxyethane (DME), dioxane and tetrahydrofuran (THF), preferably THF, at a temperature from about 0° C. to about 80° C., preferably at about room temperature. An aqueous buffer is preferably added to the reaction mixture to maintain a pH of about 7.

The aldehydes formed in the foregoing reaction can be converted into the corresponding compounds of formula I by reductive amination using, as the amine, a compound of the formula

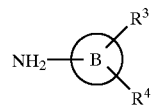

XI

The reductive amination can be carried out at a temperatures ranging from about 0° C. to about 150° C., preferably from about 20° C. to about 100° C., using any of a variety of reducing agents, for example, sodium cyanoborohydride (NaBH$_3$CN), sodium triacetoxyborohydride (NaBH(OAc)$_3$), or sodium borohydride (NaBH$_4$), in a solvent such as methylene chloride, 1,2-dichlorethane, toluene, benzene, acetic acid, methanol and ethanol. The preferred solvent will vary with the choice of reducing agent, as will be obvious to those of skill in the art. Reduction can also be accomplished by hydrogenation, using hydrogen gas at a pressure of about 1 to about 5 atmospheres, a catalyst selected from rhodium, palladium, palladium hydroxide and platinum oxide. Hydrogenation can also be carried out using a chemical hydrogen source such as ammonium formate or formic acid. Such transfer hydrogenation will use the same catalysts described above. The reductive amination may be optionally carried out in the presence of a dehydrating agent such as sodium sulfate, magnesium sulfate, calcium sulfate or molecular sieves.

The reductive amination described above proceeds through an imine intermediate, as depicted in Scheme 3. If so desired, the imine intermediate of formula XIII can be formed (and optionally isolated) by predehydrating the reaction mixture using an acid such as p-toluenesulfonic acid or sulfuric acid, with or without azeotropic removal of water, prior to addition of the reducing agent. Treatment of the imine of formula XIII under any of the previously described conditions provides the corresponding compound of formula I.

Scheme 4 illustrates an alternate method of preparing compounds of the formula II from those of formula V. The compounds of formula II, so formed, can then be converted into the desired compounds of formula I using the procedure illustrated in Scheme 2 and described above. Referring to Scheme 4, a compound of the formula V is reacted with a coupling reagent, an amine of the formula VIII, as described above, and a base in a reaction inert solvent to form a compound of the formula VI. Examples of suitable coupling reagents that activate the carboxylic functionality are dicyclohexylcarbodiimide, N-3-dimethylaminopropyl-N'-ethylcarbodiimide, 2-ethoxy-1-ethoxycarbonyl-1,2-dihydroquinoline(EEDQ), carbonyl diimidazole (CDI), and diethylphosphorylcyanide. Suitable bases include dimethylaminopyridine (DMAP) and triethylamine. Dimethylaminopyridine is preferred. A catalyst such as hydroxybenzotriazole (HBT) may also be used. The coupling is conducted in an inert solvent, preferably an aprotic solvent. Suitable solvents include acetonitrile, dichloromethane, dichloroethane, and dimethylformamide. The preferred solvent is dichloromethane. The temperature of the aforesaid reaction is generally from about −30 to about 80° C., and is preferably about 0 to about 25° C.

The compound of formula VI can be converted into a compound of the formula VII by reaction with acetyl chloride or acetic anhydride in the presence of a base (e.g., a trialkylamine such as triethylamine or tributylamine, dimethylaminopyridine or potassium carbonate) in a reaction inert solvent. Suitable solvents include methylene chloride, tetrahydrofuran and chloroform, preferably methylene chloride. Preferably, triethylamine is used as the base. This reaction is generally carried at a temperature from about 0° C. to about 35° C. for about 1 hour to about 10 hours, preferably at about 30° C. for about 3 hours.

The compound of formula VII is cyclized to a compound of formula II by reaction with triphenylphosphine, a base, and a dialkyl azodicarboxylate in a reaction inert solvent. Examples of bases that can be used in this reaction are pyridine, triethylamine and 4-dimethylaminopyridine, with 4-dimethylaminopyridine being preferred. Appropriate solvents include dimethylformamide, tetrahydrofuran and dioxane, with dioxane being preferred. Typically, this reaction is conducted at a temperature from about 25° C. to about 125° C. for about 1 hour to about 24 hours, preferably from about 80° C. to 120° C. for about 8 to 15 hours.

Compounds of formula II can also be made according to the methods described in Miyashita, et al., *Heterocycles*, 42, 2, 691–699 (1996).

Scheme 5 illustrates a method of preparing compounds of the formula I wherein YZ is NHCH$_2$. Referring to Scheme 5, a 2-aminocarboxylic acid of the formula V is reacted with an isothiocyanate of the formula XIV to form the thione product of formula XV. This reaction is generally carried out in a solvent such as acetic acid, dioxane, tetrahydrofuran, chloroform, dichloroethane or benzene, preferably acetic acid, at a temperature from about 20° C. to about 150° C., preferably at about the reflux temperature of the solvent, for about 0.25 hours to 24 hours, generally for about 1–6 hours.

The resulting thiones of formula XV can then be converted into the chlorinated compounds of formula XVI by reaction with a chlorinating agent such as phosphorus trichloride, phosphorus pentachloride, phosphorus oxychloride, thionyl chloride, sulfuryl chloride or a mixture of one or more of these chlorinating agents, preferably a mixture of phosphorus oxychloride and phosphorus pentachloride. The reaction may be carried out without a solvent or in an inert solvent such as toluene, benzene, chloroform, dichloroethane or dimethoxyethane. Reaction without a solvent is preferred unless the reagents do not freely form a solution. This reaction is generally carried out at a temperature from about 20° C. to about 180° C., preferably from about 80° C. to 150° C. for about 0.5 to 24 hours, preferably for about 1–6 hours.

Reaction of the chlorides of formula XVI with an amine of the formula

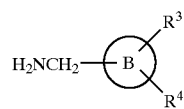

XVII yields the corresponding compounds of formula I wherein YZ is NHCH$_2$. This reaction is typically carried out in a solvent such as methanol, ethanol, propanol, isopropanol, tetrahydrofuran, dioxane or dichloroethane, with ethanol being preferred. The reaction is allowed to proceed for about 1–24 hours, at a temperature from about 20° C. to about 150° C. Preferably, the reaction is allowed to proceed for about 4–16 hours at a temperature of about 80° C. to 120 ° C.

Unless indicated otherwise, the pressure of each of the above reactions is not critical. Generally, the reactions will be conducted at a pressure of about one to about three atmospheres, preferably at ambient pressure (about one atmosphere).

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form nontoxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

The compounds of the formula I and the pharmaceutically acceptable salts thereof (hereinafter, also referred to as the active compounds of the invention) are useful for the treatment of neurodegenerative, psychotropic and drug and alcohol induced central and peripheral nervous system disorders and are potent AMPA receptor antagonists. The active compounds of the invention may therefore be used in the treatment or prevention of stroke, cerebral ischemia, spinal cord trauma, head trauma, Alzheimer's Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), ocular damage, retinopathy, retinal neuropathy, tinnitus, idiopathic and drug induced Parkinson's Disease, anxiety, emesis, brain edema, chronic or acute pain, tardive dyskinesia and cerebral deficits subsequent to cardiac bypass surgery and grafting.

The in vitro and in vivo activity of the compounds of the invention for AMPA receptor antagonism can be determined by methods available to one of ordinary skill in the art. One method for determining the activity of the compounds of the invention is by inhibition of pentylenetetrazol (PTZ)-induced seizures. Another method for determining the activity of the compounds of the invention is by blockade of AMPA receptor activation-induced $^{45}Ca^{2+}$ uptake.

One specific method for determining inhibition of pentylenetetrazol (PTZ)-induced seizures is as follows. The activity of the compounds of the invention for inhibition of pentylenetetrazol (PTZ)-induced seizures in mice can be determined according to the following procedure. This assay examines the ability of compounds to block seizures and death produced by PTZ. Measures taken are latency to clonic and tonic seizures, and death. ID$_{50}$s are determined based on percent protection.

Male CD-1 mice from Charles River, weighing 14–16 g on arrival and 25–35 g at the time of testing, serve as subjects for these experiments. Mice are housed 13 per cage under standard laboratory conditions on a L:D/7 a.m.: 7 p.m. lighting cycle for at least 7 days prior to experimentation. Food and water are available ad libitum until the time of testing.

All compounds are administered in a volume of 10 ml/kg. Drug vehicles will depend on compound solubility, but screening will typically be done using saline, distilled water, or E:D:S/5:5:90 (5% emulphor, 5% DMSO, and 90% saline) as the injection vehicle.

Mice are administered the test compounds or vehicle (i.p., s.c., or p.o.) and are placed into plexiglass cages in groups of five. At a predetermined time after these injections, mice are given an injection of PTZ (i.p., 120 mg/kg) and placed into individual plexiglass cages. Measures taken during this five minute test period are: (1) latency to clonic seizures, (2) latency to tonic seizures, and (3) latency to death. Treatment groups are compared to the vehicle-treated group by Kruskal-Wallis Anova and Mann-Whitney U tests (Statview). Percent protection is calculated for each group (number of subjects not showing seizure or death as indicated by a score of 300 secs) at each measure. $ID_{50}$'s are determined by prohibit analysis (Biostat).

Another method for determining the activity of the compounds is to determine the effect of the compounds on motor coordination in mice. This activity can be determined according to the following procedure.

Male CD-1 mice from Charles River, weighing 14–16 g on arrival and 23–35 g at the time of testing, serve as subjects for these experiments. Mice are housed 13 per cage under standard laboratory conditions on a L:D/7 a.m.: 7 p.m. lighting cycle for at least 7 days prior to experimentation. Food and water are available ad libitum until the time of testing.

All compounds are administered in a volume of 10 ml/kg. Drug vehicles will depend on compound solubility, but screening will typically be done using saline, distilled water, or E:D:S/5:5:90 (5% emulphor, 5% DMSO, and 90% saline) as the injection vehicle.

The apparatus used in these studies consists of a group of five 13.34×13.34 cm wire mesh squares suspended on 11.43 cm steel poles connected to a 165.1 cm pole which is elevated 38.1 cm above the lab bench. These wire mesh squares can be turned upside-down.

Mice are administered test compounds or vehicle (i.p., s.c., or p.o) and are placed into plexiglass cages in groups of five. At a predetermined time after these injections, mice are placed on top of the wire mesh squares and flipped so that they are suspended upside-down. During the one minute test, mice are rated 0 if they fall off the screen, 1 if they hang on upside-down, or 2 if they climb up onto the top. Treatment groups are compared to the vehicle-treated group with Kruskal-Wallis and Mann-Whitney U tests (Statview).

One specific method for determining blockade of AMPA receptor activation-induced $^{45}Ca^{2+}$ uptake is described below.

Neuronal Primary Cultures

Primary cultures of rat cerebellar granule neurons are prepared as described by Parks, T. N., Artman, L. D., Alasti, N., and Nemeth, E. F., *Modulation Of N-Methyl-D-Aspartate Receptor-Mediated Increases In Cytosolic Calcium In Cultured Rat Cerebellar Granule Cells,* Brain Res. 552, 13–22 (1991). According to this method, cerebella are removed from 8 day old CD rats, minced into 1 mm pieces and incubated for 15 minutes at 37° C. in calcium-magnesium free Tyrode's solution containing 0.1% trypsin. The tissue is then triturated using a fine bore Pasteur pipette. The cell suspension is plated onto poly-D-lysine coated 96-well tissue culture plates at $10^5$ cells per well. Medium consists of Minimal Essential Medium (MEM), with Earle's salts, 10% heat inactivated Fetal Bovine Serum, 2 mM L-glutamine, 21 mM glucose, Penicillin-Streptomycin (100 units per ml) and 25 mM KCl. After 24 hours, the medium is replaced with fresh medium containing 10 $\mu$M cytosine arabinoside to inhibit cell division. Cultures should be used at 6–8 DIV.

AMPA Receptor Activation-Induced $^{45}Ca^{2+}$ Uptake

The effects of drugs on AMPA receptor activation-induced $^{45}Ca^{2+}$ uptake can be examined in rat cerebellar granule cell cultures. Cultures in 96 well plates are preincubated for approximately 3 hours in serum free medium and then for 10 minutes in a $Mg^{2+}$-free balanced salt solution (in mM: 120 NaCl, 5 KCl, 0.33 $NaH_2PO_4$ 1.8 $CaCl_2$, 22.0 glucose and 10.0 HEPES at pH 7.4) containing 0.5 mM DTT, 10 uM glycine and drugs at 2× final concentration. The reaction is started by rapid addition of an equal volume of the balanced salt solution containing 100 $\mu$M of the AMPA receptor agonist kainic acid and $^{45}Ca^{2+}$ (final specific activity 250 Ci/mmol). After 10 minutes at 25° C., the reaction is stopped by aspirating the $^{45}Ca^{2+}$-containing solution and washing the cells 5× in an ice cold balanced salt solution containing no added calcium and 0.5 mM EDTA. Cells are then lysed by overnight incubation in 0.1% Triton-X100 and radioactivity in the lysate is then determined. All of the compounds of the invention, that were tested, had $IC_{50}$s of less than 5 $\mu$M.

The compositions of the present invention may be formulated in a conventional manner using one or more pharmaceutically acceptable carriers. Thus, the active compounds of the invention may be formulated for oral, buccal, transdermal (e.g., patch), intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., stroke) is 0.01 to 50 mg/kg of the active ingredient per unit dose which could be administered, for example, 1 to 4 times per day.

Aerosol formulations for treatment of the conditions referred to above (e.g., stroke) in the average adult human are preferably arranged so that each metered dose or "puff" of aerosol contains 200 µg to 1000 µg of the compound of the invention. The overall daily dose with an aerosol will be within the range 100 µg to 10 mg. Administration may be several times daily, for example 2, 3, 4 or 8 times, giving for example, 1, 2 or 3 doses each time.

The following Examples illustrate the preparation of the compounds of the present invention. Commercial reagents were utilized without further purification. Melting points are uncorrected. All NMR data were recorded at 250, 300 or 400 MHz in deuterochloroform unless otherwise specified and are reported in parts per million (δ) and are referenced to the deuterium lock signal from the sample solvent. All non-aqueous reactions were carried out in dry glassware with dry solvents under an inert atmosphere for convenience and to maximize yields. All reactions were stirred with a magnetic stirring bar unless otherwise stated. Unless otherwise stated, all mass spectra were obtained using chemical impact conditions. Ambient or room temperature refers to 20–25° C. Melting points are uncorrected.

EXAMPLE 1

2-{[3-(2-Chloro-pyridin-3-yl)-6-fluoro-4-oxo-3,4-dihydro-quinazolin-2-ylmethyl]-amino}-benzonitrile A mixture of 3-(2-chloro-pyridin-3-yl)-6-fluoro-3,4-dihydro-quinazolin-4-one-2-carboxaldehyde hydrate (0.164 g, 0.51 mmol), toluene (25 mL), anthranilonitrile (0.135 g, 1.12 mmol), and glacial acetic acid (0.064 mL, 1.12 mmol) was refluxed 6 hours with azeotropic removal of water. The mixture was cooled to ambient temperature and anthranilonitrile (0.135 g, 1.12 mmol) and glacial acetic acid (1 mL) were added. The reaction was refluxed 24 hours. Catalytic p-toluenesulfonic acid (a couple mg) was added and the reaction was refluxed a further 24 hours. The mixture was cooled to ambient temperature, diluted with ethyl acetate and extracted with saturated aqueous bicarbonate, water and brine. The organic layer was dried over sodium sulfate and concentrated to afford 0.378 g of the crude imine as a dark oil. The imine had $R_f$ 0.15 on silica gel tic developed with 30% ethyl acetate/hexane, UV detection.

The crude imine (0.378 g) was dissolved in ethanol (10 mL) and 10% palladium on carbon (0.14 g) and formic acid (0.5 mL) were added. The mixture was stirred at ambient temperature overnight. The mixture was filtered through celite and the filtrate was concentrated. The residue was taken up in 1 mL of 50% ethyl acetate/hexane and applied to a silica gel column (1×4 inches, packed with 25% ethyl acetate/hexane) for flash chromatographic purification. Elution proceeded as follows: 25% ethyl acetate/hexane (50 mL), unweighed recovered anthranilonitrile (50 mL), trace impurities (250 mL), and yielded 0.112 g (54%) of 2-{[3-(2-chloro-pyridin-3-yl)-6-flouro-4-oxo-3,4-dihydro-quinazolin-2-ylmethyl]-amino}-benzonitrile as an oil which solidified on standing and had: mp 183–187° C.; $^1$H NMR δ 8.66 (dd, J=1.8, 4.8 Hz, 1 H), 7.95–7.86 (m, 2 H), 7.79 (dd, J=1.8, 7.8 Hz, 1 H), 7.60–7.53 (m, 2 H), 7.43 (dd, J=1.5, 7.7 Hz, 1 H), 7.33 (t, J=8 Hz, 1 H), 6.73 (t, J=7 Hz, 1 H), 6.42 (d, J=8.4 Hz, 1 H), 6.02 (br s, 1 H), 3.95 (ABq, $\Delta v_{1-3}$=4.5 Hz, J=2 Hz, 2 H); APCI MS m/z=406 ($P^{+1}$).

EXAMPLE 2

3-{[3-(2-Chloro-phenyl)-6-fluoro-4-oxo-3,4-dihydro-quinazolin-2-ylmethyl]-amino}-benzonitrile A mixture of 3-(2-chloro-phenyl)-6-fluoro-3,4-dihydro-quinazolin-4-one-2-carboxaldehyde (0.150 g, 0.50 mmol), glacial acetic acid (10 mL), 3-aminobenzonitrile (0.050 g, 0.42 mmol), and anhydrous sodium sulfate (0.71 g, 5 mmol) was stirred at ambient temperature overnight. Tlc indicated that the imine had formed ($R_f$=0.43 on silica gel tic developed with 30% ethyl acetate/hexane, UV detection). Sodium triacetoxyborohydride (0.267 g, 1.26 mmol) was added and the reaction was allowed to stir over the weekend (72 hours). The mixture was poured into saturated aqueous bicarbonate and repeatedly extracted with ethyl acetate. The combined organic layer was dried over magnesium sulfate and concentrated to afford a yellow solid. This solid was triturated with 50% ethyl ether/isopropyl ether to give 0.133 g (78%) of 3-{[3-(2-chloro-phenyl)-6-fluoro-4-oxo-3,4-dihydro-quinazolin-2-ylmethyl]-amino}-benzonitrile as an off white solid which had: mp 225–228° C.; $^1$H NMR δ 7.93 (dd, J=3, 8 Hz, 1 H), 7.87 (dd, J=4.5, 8.5 Hz, 1 H), 7.70 (dd, J=1.5, 7.5 Hz, 1 H), 7.62–7.52 (m, 4 H), 7.40 (dd, J=1.5, 7.5 Hz, 1 H), 7.20 (t, J=8 Hz, 1 H), 6.97 (d, J=7.5 Hz, 1 H), 6.80 (dd, J=2, 8 Hz, 1 H), 6.66 (s, 1 H), 3.88 (ABq, $\Delta v_{1-3}$=39.5 Hz, J=17 Hz, 2 H). Analysis calculated for $C_{22}H_{14}ClFN_4O \cdot 0.5 H_2O$: C, 63.85; H, 3.65; N, 13.54. Found: C, 63.90; H, 3.31; N, 13.46.

EXAMPLE 3

3-(2-Chloro-phenyl)2-[(3-diethylaminomethyl-phenylamino)-methyl]-6-fluoro-3H-quinazolin-4-one A mixture of 3-(N,N-diethylamino-methyl)-aniline (0.080 g, 0.45 mmol) and 3-(2-chloro-phenyl)-6-fluoro-3,4-dihydro-quinazolin-4-one-2-carboxaldehyde (0.150 g, 0.50 mmol in methanol (15 mL) was refluxed 48 hours to form the imine intermediate. The reaction was cooled to ambient temperature and sodium borohydride (0.038 g, 1 mmol) was added and the mixture was refluxed for 24 hours. Additional sodium borohydride (0.038 g, 1 mmol) was added and refluxing was continued 2 hours. Sodium borohydride (0.038 g, 1 mmol) was added and the mixture was refluxed for an additional 18 hours. The reaction was allowed to stir overnight at ambient temperature. Water was added and the mixture was stirred for 30 minutes. The reaction mixture was repeatedly extracted with ethyl acetate. The combined organic phase was washed with saturated aqueous bicarbonate and brine. The organic phase was dried over magnesium sulfate and concentrated to a dark yellow oil. The oil was flash chromatographed on silica gel (30 g), with elution proceeding as follows: 20% ethyl acetate/hexane (150 mL), nil; (50 mL), 0.015 g unknown product; (75 mL), nil; (125 mL), 0.01 g, 3-(2-chloro-phenyl)-6-fluoro-3,4-dihydro-quinazolin-4-one-2-methanol; (350 mL), nil; 30% ethyl acetate/hexane (300 mL), nil; 50% ethyl acetate/hexane (450 mL), nil; (350 mL) and chloroform (50 mL), 0.016 g (0.8%) of 3-(2-chloro-phenyl)-2-[(3-diethylaminomethyl-phenylamino)-methyl]-6-fluoro-3H-quinazolin-4-one as a viscous yellow oil which had: $^1$H NMR δ 7.92 (dd, J=3, 8 Hz, 1 H), 7.82 (dd, J=5, 9 Hz, 1 H), 7.66–7.65 (m, 1 H), 7.57–7.46 (m, 4 H), 7.14 (t, J=8 Hz, 1 H), 7.08 (s, 1 H), 6.70 (d, J=7 Hz, 1 H), 6.59 (d, J=8 Hz, 1 H), 5.28 (s, 1 H), 4.06–3.81 (m, 4 H), 3.46 (q, J=7 Hz, 4 H), 1.19 (t, J=7 Hz, 6 H); APCI MS m/z=465.1 (P$^{+1}$).

EXAMPLE 4

3-(2-Chloro-phenyl)-6-fluoro-2-(pyrimidin-2-ylaminomethyl)-3H-quinazolin-4-one

A mixture of 3-(2-chloro-phenyl)-6-fluoro-3,4-dihydro-quinazolin-4-one-2-carboxaldehyde (0.200 g, 0.66 mmol), methanol (20 mL), and 2-aminopyrimidine (0.059 g, 0.62 mmol) was refluxed 29 hours. The mixture was cooled to room temperature and 10% palladium on carbon (0.236 g) and formic acid (1.1 mL) were added. The mixture was allowed to stir at ambient temperature overnight. The reaction was treated with 6 N sodium hydroxide to adjust the pH to 10. The mixture was filtered through celite and the pad was washed with ethyl acetate. The filtrate was dried over magnesium sulfate and concentrated. The residue was flash chromatographed on silica gel (20 g) with elution proceeding as follows: 10% ethyl acetate/hexane (500 mL), nil; 20% ethyl acetate/hexane (250 mL), unweighed impurity, 20% ethyl acetate/hexane (100 mL), mixed fraction, unweighed; 20% ethyl acetate/hexane (150 mL) and 30% ethyl acetate/hexane (150 mL), unweighed 3-(2-chloro-phenyl)-6-fluoro-3,4-dihydro-quinazolin-4-one-2-methanol (a side product). Elution was continued: 30% ethyl acetate/hexane 410 mL), nil; 40% ethyl acetate/hexane (450 mL), nil; 40% ethyl acetate/hexane (50 mL) and 50% ethyl acetate/hexane (450 mL), 0.028 g (8%) of 3-(2-Chloro-phenyl)-6-fluoro-2-(pyrimidin-2-ylaminomethyl)-3H-quinazolin-4-one as a white solid which had: mp 182–185° C.; $^1$H NMR δ 8.29 (d, J=5 Hz, 2 H), 7.92 (dd, J=3, 8 Hz, 1 H), 7.82 (dd, J=5, 9 Hz, 1 H), 7.66–7.64 (m, 1 H), 7.55–7.49 (m, 3 H), 7.40–7.38 (m, 1 H), 6.63 (t, J=5 Hz, 1 H), 4.28 (dd, J=4.5, 18 Hz, 1 H), 4.11 (dd, J=4, 18 Hz, 1 H). Analysis calculated for $C_{19}H_{11}ClFN_5O.0.75$ $H_2O$: C, 58.05; H, 3.20; N, 17.81. Found: C, 58.06; H, 3.25; N, 17.33. APCI MS m/z=382 (P$^{+1}$).

EXAMPLE 5

3-(2-Chloro-pyridin-3-yl)-6-fluoro-2-(m-tolylamino-methyl)-3H-quinazolin-4-one

A mixture of 3-(2-chloro-pyridin-3-yl)-6-fluoro-3,4-dihydro-quinazolin-4-one-2-carboxaldehyde (0.150 g, 0.49 mmol) and 3-diethylaminomethylaniline (0.073 g, 0.41 mmol) in methanol (10 mL) were stirred at ambient temperature for 72 hours and then concentrated to afford 0.252 g of yellow solid imine which had: APCI MS m/z=464 (P$^{+1}$). The crude imine was dissolved in ethanol (10 mL) and 10% palladium on carbon (0.252 g) and formic acid (0.90 mL, 24.3 mmol) were added. The mixture was stirred at ambient temperature for 6 hours. Solid potassium carbonate (0.5 g) was added and the mixture was stirred 1 hour longer. The reaction was filtered through celite and the pad was washed with ethyl acetate. The filtrate was concentrated. The residue was taken up in ethyl acetate and washed with saturated bicarbonate and brine, dried over magnesium sulfate, and concentrated to a yellow oil. The oil was flash chromatographed on silica gel (15 g) with elution proceeding as follows: 10% ethyl acetate/hexane (300 mL), nil; 20% ethyl acetate/hexane (400 mL), nil; 20% ethyl acetate/hexane (150 mL), 0.033 g (20%) of 3-(2-chloro-pyridin-3-yl)-6-fluoro-2-(m-tolylamino-methyl)-3H-quinazolin-4-one as a white solid which had: mp 177–180° C.; $^1$H NMR δ 8.63 (dd, J=2, 5 Hz, 1 H), 7.92 (dd, J=3, 8 Hz, 1 H), 7.83 (dd, J=5, 9 Hz, 1 H), 7.76 (dd, J=2, 8 Hz, 1 H), 7.58–7.50 (m, 2 H), 7.05 (t, J=8 Hz, 1 H), 6.61 (d, J=7 Hz, 1 H), 6.43–6.39 (m, 2 H), 3.90 (ABq, Δν$_{1-3}$=23 Hz, J=7 Hz, 2 H), 2.25 (s, 3 H). Analysis calculated for $C_{21}H_{18}ClFN_4O.0.25$ $H_2O$: C, 63.16; H, 4.16; N, 14.03. Found: C, 63.06; H, 4.28; N, 13.72.

EXAMPLE 6

3-(2-Chloro-pyridin-3-yl)-6-fluoro-2-[(6-methyl-pyridin-2-ylamino)-methyl]-3H-quinazolin-4 one To a mixture of 3-(2-chloro-pyridin-3-yl)-6-fluoro-3,4-dihydro-quinazolin-4-one-2-carboxaldehyde (0.20 g, 0.66 mmol) and 2-amino-6-methylpyridine (0.0476 g, 0.44 mmol) in methanol (10 mL) was added acetic anhydride (0.042 mL, 0.44 mmol). The mixture was gently refluxed overnight, cooled to ambient temperature and diluted with saturated aqueous bicarbonate. This aqueous mixture was repeatedly extracted with ethyl acetate. The combined organic phase was washed with saturated aqueous bicarbonate and brine, dried over magnesium sulfate and concentrated to afford 0.303 g of crude imine as a yellow oil. The imine was dissolved in ethanol (10 mL) and 10% palladium on carbon (0.17 g) and formic acid (0.75 mL) were added. The mixture was stirred overnight at ambient temperature. Sodium bicarbonate (0.5 g) was added. The mixture was stirred for 1 additional hour, and then filtered through celite and the pad was washed with ethanol and ethyl acetate. The filtrate was concentrated to a colorless solid. This solid was triturated with ethyl acetate causing the product to dissolve into the solvent. The solution was concentrated and flash chromatographed on silica gel (20 g). Elution proceeded as follows: 50% ethyl acetate/hexane (350 mL), nil; 50% ethyl acetate/hexane (550 mL), mixture of desired product and 3-(2-chloro-pyrid-3-yl)-6-fluoro-3,4-dihydro-quinazolin-4-one-2-methanol as a white solid. This mixture was triturated with 50% isopropyl ether/hexane to afford 0.025 g (14%) of 3-(2-chloro-pyridin-3-yl)-6-fluoro-2-[(6-methyl-pyridin-2-ylamino)-methyl]-3H-quinazolin-4-one as a white solid which had: mp 190–195° C.; $^1$H NMR δ 8.56 (dd, J=1, 5 Hz, 1 H), 7.91 (dd, J=3, 8 Hz, 1 H), 7.80–7.76 (m, 2 H), 7.53 (dt, J=3, 8 Hz, 1 H), 7.46 (dd, J=5, 8 Hz, 1 H), 7.29 (t, J=8 Hz, 1 H), 6.44 (d, J=7 Hz, 1 H), 6.24 (d, J=8 Hz, 1 H), 5.64 (s, 1 H), 4.27 (dd, J=6, 17 Hz, 1 H), 4.10 (dd, J=5, 17 Hz, 1 H), 2.03 (s, 3 H). Analysis calculated for $C_{20}H_{15}ClFN_5O.H_2O$: C, 58.05; H, 4.14; N, 16.92. Found: C, 58.45; H, 3.71; N, 16.53.

EXAMPLE 7

3-(2-Chloro-phenyl)-6-fluoro-2-(pyridin-2-ylaminomethyl)-3H-quinazolin-4-one Hydrochloride A mixture of 3-(2-chloro-phenyl)-6-fluoro-3,4-dihydro-quinazolin-4-one-2-carboxaldehyde (0.20 g, 0.66 mmol), 2-aminopyridine (0.069 g, 0.73 mmol) and acetic acid (0.075 mL, 1.32 mmol) in toluene (25 mL) was for refluxed 5 hours with azeotropic removal of water. The reaction was cooled to ambient temperature and extracted with saturated aqueous bicarbonate. The phases were separated and the organic phase was dried over sodium sulfate and concentrated to afford the crude imine as a brown foam which had: mp 158–162° C. A portion of this imine (0.10 g, 0.264 mmol) was dissolved in ethanol (10 mL) and 10% palladium on carbon (0.10 g) and formic acid (0.45 mL, 11.9 mmol) were added. The mixture was stirred at ambient temperature for 4 hours, and then filtered through celite and the pad was rinsed with ethyl acetate and water. The layers were separated from the two phase filtrate and the organic layer was washed with saturated aqueous bicarbonate, dried over magnesium sulfate and concentrated to afford 0.065 g (65%) the free base product as a brown oil which had: $^1$H NMR δ 8.02 (d, J=4 Hz, 1 H), 7.94 (dd, J=5, 9 Hz, 1 H), 7.66–7.61 (m, 1 H), 7.57–7.36 (m, 6 H), 6.58 (t, J=5 Hz, 1 H), 6.50 (d, J=8 Hz, 1 H), 5.83 (br s, 1 H), 4.25 (dd, J=5, 18 Hz, 1 H), 4.03 (dd, J=4, 18 Hz, 1 H); APCI MS m/z=381.1 ($P^{+1}$). The free base was dissolved in ether (15 mL) and chilled to 0° C. Ethereal hydrochloric acid (0.20 mL, 0.2 mmol, approximately 1 N) was added to the solution. The precipitate was collected and dried to afford 0.025 g of 3-(2-chloro-phenyl)-6-fluoro-2-(pyridin-2-ylaminomethyl)-3H-quinazolin-4-one hydrochloride as an amorphous solid which had: mp 90–100° C.

EXAMPLE 8

3-(2-Chloro-pyridin-3-yl)-6-fluoro-2-[(3-pyrrolidin-1-ylmethyl-phenylamino)-methyl]-3H-quinazoline-4-one A mixture of 3-(2-chloro-pyridin-3-yl)-6-fluoro-3,4-dihydro-quinazolin-4-one-2-carboxaldehyde (0.150 g, 0.49 mmol), 3-pyrrolidin-1-ylmethylaniline (0.044 g, 0.25 mmol), and acetic acid (0.14 mL, 2.45 mmol) in dichloroethane (10 mL) was chilled to 0° C. and sodium triacetoxyborohydride (0.312 g, 1.47 mmol) was added. The reaction was stirred for 1 hour at 0° C. and then allowed to warm to ambient temperature. The reaction was quenched by addition of saturated aqueous bicarbonate and continued stirring for 30 minutes. The phases were separated and the aqueous layer was extracted with methylene chloride. The combined organic phase was washed with brine, dried over magnesium sulfate and concentrated. The residue was flash chromatographed on silica gel (45 g) with elution proceeding as follows: 10% methanol/0.5% ammonium hydroxide/chloroform (200 mL), nil; (50 mL), unweighed impurity; (25 mL), nil; (75 mL), unweighed mixed fraction; (200 mL), 0.010 g (8%) of 3-(2-chloro-pyridin-3-yl)-6-fluoro-2-[(3-pyrrolidin-1-ylmethyl-phenylamino)-methyl]-3H-quinazolin-4-one as a pale yellow solid which had: $^1$H NMR δ 8.60 (d, J=5 Hz, 1 H), 7.80 (t, J=5 Hz, 1 H), 7.76 (d, J=9 Hz, 1 H), 7.71 (dd, J=3, 9 Hz, 1 H), 7.58–7.50 (m, 2 H), 7.35 (dd, J=5, 8 Hz, 1 H), 7.14–7.08 (m, 2 H), 6.80 (dd, J=4, 9 Hz, 1 H), 4.44 (s, 1 H), 3.90–3.65 (m, 4 H), 2.79 (br s, 4 H), 1.90 (br s, 4 H); APCI MS m/z=464 ($P^{+1}$).

EXAMPLE 9

6-Fluoro-3-(2-methyl-pyridin-3-yl)-2-[(3-pyrrolidin-1-ylmethyl-phenylamino)-methyl]-3H-quinazolin-4-one A mixture of 3-(2-methyl-pyridin-3-yl)-6-fluoro-3,4-dihydro-quinazolin-4-one-2-carboxaldehyde (0.158 g, 0.56 mmol), 3-pyrrolidin-1-ylmethylaniline (0.050 g, 0.28 mmol), and acetic acid (0.16 mL, 2.8 mmol) in dichloroethane (15 mL) was chilled to 0° C. and sodium triacetoxyborohydride (0.297 g, 1.4 mmol) was added. The reaction was stirred for 1 hour at 0° C. and then allowed to warm to ambient temperature and stirred for 16 hours. The reaction was quenched by addition of saturated aqueous bicarbonate and continued stirring for 30 minutes. The phases were separated and the aqueous layer was extracted with methylene chloride. The combined organic phase was washed with brine, dried over magnesium sulfate and concentrated. The residue was flash chromatographed on silica gel (35 g) with elution proceeding as follows: 10% methanol/0.5% ammonium hydroxide/chloroform (50 mL), nil; (75 mL), unweighed impurity; (50 mL), unweighed 3-(2-methyl-pyridin-3-yl)-6-fluoro-3,4-dihydro-quinazolin-4-one-2-methanol; (50 mL), unweighed mixed fraction; (100 mL), 0.031 g (25%) of 3-(2-methyl-pyridin-3-yl)-6-fluoro-2-[(3-pyrrolidin-1-ylmethyl-phenylamino)-methyl]-3H-quinazolin-4-one as a yellow foam which had: $^1$H NMR δ 8.72 (d, J=5 Hz, 1 H), 7.92 (dd, J=3, 8 Hz, 1 H), 7.82 (dd, J=5, 9 Hz, 1 H), 7.58–7.52 (m, 2 H), 7.39 (dd, J=5, 8 Hz, 1 H), 7.08 (t, J=8 Hz, 1 H), 6.67–6.64 (m, 2 H), 6.37 (d, J=8 Hz, 1 H), 5.10 (s, 1 H), 3.90 (dd, J=4.5, 17 Hz, 1 H), 3.70 (dd, J=5, 17 Hz, 1 H), 3.56 (ABq, $\Delta v_{1-3}$=21 Hz, J=12.5 Hz, 2 H), 2.54 (s, 4 H), 2.36 (s, 3 H), 1.78 (s, 4 H); APCI MS m/z=444 ($P^{+1}$).

EXAMPLE 10

3-(2-Chloro-phenyl)-6-fluoro-2-[(2-fluoro-benzylamino)-methyl]-3H-quinazolin-4-one A mixture of 3-(2-chloro-phenyl)-6-fluoro-3,4-dihydro-quinazolin-4-one-2-carboxaldehyde (0.20 g, 0.66 mmol), 2-fluorobenzylamine (0.038 mL, 0.33 mmol), and acetic acid (0.19 mL, 3.3 mmol) in dichloroethane (10 mL) was chilled to 0° C. and sodium triacetoxyborohydride (0.350 g, 1.65 mmol) was added. The reaction was stirred for 1 hour at 0° C. and then allowed to warm to ambient temperature and stirred 16 hours. The reaction was quenched by addition of saturated aqueous bicarbonate and continued stirring for 30 minutes. The phases were separated and the aqueous layer was extracted with methylene chloride. The combined organic phase was washed with brine, dried over magnesium sulfate and concentrated. The residue was flash chromatographed on silica gel (30 g) with elution proceeding as follows: 30% ethyl acetate/hexane (100 mL), nil; (50 mL), unweighed impurity; (100 mL), nil; (125 mL), unweighed impurity; (150 mL), unweighed 3-(2-chloro-phenyl)-6-fluoro-3,4-dihydro-quinazolin-4-one-2-methanol; (450 mL), unweighed 3-(2-chloro-phenyl)-6-fluoro-2-[(2-fluoro-benzylamino)-methyl]-3H-quinazolin-4-one as a pale pink solid which had: mp 140° C.; $^1$H NMR δ 7.89 (dd, J=3, 8 Hz, 1 H), 7.76 (dd, J=4, 9 Hz, 1 H), 7.58 (dd, J=2, 8 Hz, 1 H), 7.53–7.41 (m, 4 H), 7.35–7.30 (m, 2 H), 7.07 (t, J=8 Hz, 1 H), 6.99 (t, J=10 Hz, 1 H), 3.89 (ABq, $\Delta v_{1-3}$=21 Hz, J=13 Hz, 2 H), 3.46 (ABq, $\Delta v_{1-3}$=31 Hz, J=17 Hz, 2 H); APCI MS m/z=412 ($P^{-1}$).

EXAMPLE 11

N-(3-{[3-(2-Chloro-phenyl)-6-fluoro-4-oxo-3,4-dihydro-quinazolin-2-ylmethyl]-amino}-phenyl)-acetamide A mixture of 3-(2-chloro-phenyl)-6-fluoro-3,4-dihydro-quinazolin-4-one-2-carboxaldehyde (0.20 g, 0.66 mmol), 3-aminoacetanilide hydrochloride (0.062 g, 0.33 mmol), triethylamine (0.092 mL, 0.66 mmol), and acetic acid (0.19 mL, 3.3 mmol) in dichloroethane (10 mL) was chilled to 0° C. and sodium triacetoxyborohydride (0.350 g, 1.65 mmol) was added. The reaction was stirred for 1 hour at 0° C. and then allowed to warm to ambient temperature and stirred 16 hours. The reaction was quenched by addition of saturated aqueous bicarbonate and continued stirring for 30 minutes. The phases were separated and the aqueous layer was extracted with methylene chloride. The combined organic phase was washed with brine, dried over magnesium sulfate and concentrated. The residue triturated with 50% isopropyl ether/hexane to afford 0.035 g (24%) of N-(3-{[3-(2-Chloro-phenyl)-6-fluoro-4-oxo-3,4-dihydro-quinazolin-2-ylmethyl]-amino}-phenyl)-acetamide as a yellow solid which had: $^1$H NMR δ 7.92 (dd, J=3, 8 Hz, 1 H), 7.86 (dd, J=5, 9 Hz, 1 H), 7.67–7.64 (m, 1 H), 7.56–7.48 (m, 4 H), 7.40 (dd, J=2, 7 Hz, 1 H), 7.32 (d, J=7 Hz, 1 H), 7.13 (s, 1 H), 7.06 (t, J=8 Hz, 1 H), 6.65 (d, J=8 Hz, 1 H), 6.28 (d, J=8 Hz, 1 H), 3.89 (ABq, $\Delta v_{1-3}$=49 Hz, J=17 Hz, 2 H), 2.12 (s, 3 H); APCI MS m/z=437 ($P^{+1}$).

EXAMPLE 12

3-(2-Chloro-phenyl)-6-fluoro-2-[(3-pyrrolidin-1-ylmethyl-phenylamino)-methyl]-3H-quinazolin-4-one A mixture of 3-(2-chloro-phenyl)-6-fluoro-3,4-dihydro-quinazolin-4-one-2-carboxaldehyde (0.50 g, 1.65 mmol), 3-pyrrolidin-1-ylmethylaniline (0.291 g, 1.65 mmol) and anhydrous sodium sulfate (2.3 g, 16.5 mmol) in dichloroethane (20 mL) was refluxed for 24 hours. The mixture was diluted with water and stirred for 20 min. The phases were separated and the organic phase was washed with saturated aqueous bicarbonate and brine, dried over magnesium sulfate and concentrated to afford 0.61 g of crude imine. The imine was dissolved in ethanol (20 mL) and 10% palladium on carbon (0.61 g) and formic acid (2.6 mL, 69.7 mmol) were added. The reaction was stirred at ambient temperature for 3 hours and then saturated aqueous sodium bicarbonate was added. The mixture was filtered through celite and the filtrate was concentrated to remove most of the ethanol. The milky aqueous residue was extracted with ethyl acetate. The organic phase was washed with water and brine, dried over magnesium sulfate, and concentrated. The residue was flash chromatographed on silica gel (45 g) with elution proceeding as follows: 10% methanol/0.5% ammonium hydroxide/chloroform (200 mL), nil; (200 mL), 0.322 g (53%) of 3-(2-chloro-phenyl)-6-fluoro-2-[(3-pyrrolidin-1-ylmethyl-phenylamino)-methyl]-3H-quinazolin-4-one as an off-white foam which had: mp 105–110° C.; $^1$H NMR δ 7.92 (dd, J=3, 8 Hz, 1 H), 7.80 (dd, J=5, 9 Hz, 1 H), 7.67–7.65 (m, 1 H), 7.59–7.50 (m, 3 H), 7.40–7.38 (m, 1 H), 7.08 (t, J=8 Hz, 1 H), 6.69–6.65 (m, 2 H), 6.40 (d, J=8 Hz, 1 H), 5.13 (s, 1 H), 3.94 (dd, J=5, 17 Hz, 1 H), 3.81 (dd, J=4.5, 17 Hz, 1 H), 3.59 (br s, 2 H), 2.58 (br s, 4 H), 1.80 (br s, 4 H). Analysis calculated for $C_{26}H_{24}ClFN_4O\cdot H_2O$: C, 64.93; H, 5.45; N, 11.65. Found: C, 65.09; H, 5.04; N, 11.48.

EXAMPLE 13

2-{[3-(2-Chloro-phenyl)-6-fluoro-4-oxo-3,4-dihydro-quinazolin-2-ylmethyl]-amino}-nicotinonitrile A mixture of 3-(2-chloro-phenyl)-6-fluoro-3,4-dihydro-quinazolin-4-one-2-carboxaldehyde (0.439 g, 1.45 mmol), 2-aminonicotinonitrile (0.150 g, 1.26 mmol) and anhydrous sodium sulfate (2.1 g, 14.5 mmol) in acetic acid (10 mL) was stirred at ambient temperature for 24 hours. The mixture was now warmed to 80° C. for 24 hours. The reaction was cooled to ambient temperature and sodium triacetoxyborohydride (1.3 g, 6.13 mmol) was added portionwise. The reaction was stirred for 16 hours and then quenched by carefully pouring it into a mixture of saturated aqueous sodium bicarbonate (150 mL) and ethyl acetate (20 mL). This quenching solution was stirred 30 min. The phases were separated and the organic layer was washed with brine, dried over magnesium sulfate and concentrated. The residue was flash chromatographed on silica gel (50 g) with elution proceeding as follows: 20% ethyl acetate/hexane (350 mL), nil; 30% ethyl acetate/hexane (350 mL), unweighed 3-(2-chloro-phenyl)-6-fluoro-3,4-dihydro-quinazolin-4-one-2-methanol; 40% ethyl acetate/hexane (400 mL), impure product. This partially purified product was flash chromatographed on silica gel (20 g) with elution proceeding as follows: 5% ethyl acetate/hexane (1000 mL), nil; 10% ethyl acetate/hexane (1000 mL), nil; 15% ethyl acetate/hexane (750 mL), nil; (500 mL), unweighed impurity; 20% ethyl acetate/hexane (1000 mL), nil; (1000 mL), unweighed impurity; 30% ethyl acetate/hexane (600 mL), 0.050 g (10%) of 2-{[3-(2-chloro-phenyl]-6-fluoro-4-oxo-3,4-dihydro-quinazolin-2-ylmethyl]-amino}-nicotinonitrile as a light tan solid which had: mp 145–150° C.; $^1$H NMR δ 8.16 (d, J=5 Hz, 1 H), 7.93 (dd, J=3, 8 Hz, 1 H), 7.84 (dd, J=5, 9 Hz, 1 H), 7.71–7.63 (m, 2 H), 7.56–7.51 (m, 3 H), 7.40 (d, J=7 Hz, 1 H), 6.85 (s, 1 H), 6.62 (dd, J=5, 7 Hz, 1 H), 4.23 (ABq, $\Delta v_{1-3}$=74 Hz, J=19 Hz, 2 H); APCI MS m/z=406.2 ($P^{+1}$).

EXAMPLE 14

3-(2-Chloro-pyridin-3-yl)-6-fluoro-2-[(2-fluoro-phenylamino)-methyl]-3H-quinazolin-4-one A mixture of 3-(2-chloro-pyridin-3-yl)-6-fluoro-3,4-dihydro-quinazolin-4-one-2-carboxaldehyde (0.20 g, 0.66 mmol), 2-fluoroaniline (0.053 mL, 0.55 mmol) and anhydrous sodium sulfate (0.9 g, 6.6 mmol) in dichloroethane (10 mL) was refluxed for 18 hours. The reaction was concentrated and the residue was partitioned between ethyl acetate and water. The phases were separated and the organic phase was washed with saturated aqueous bicarbonate and brine, dried over magnesium sulfate and concentrated to afford 0.186 g of crude imine as a yellow foam. The imine was dissolved in ethanol (10 mL) and 10% palladium on carbon (0.186 g,) and formic acid (0.90 mL, 23.5 mmol) were added. The reaction was stirred at ambient temperature for 1.5 hours. The acid was quenched by addition of solid potassium carbonate and stirring 30 minutes. The mixture was filtered through celite and the pad was washed with ethanol and ethyl acetate. The filtrate was concentrated and the residue was taken up in ethyl acetate. This organic phase was washed with water and brine, dried over magnesium sulfate, and concentrated. The residue was flash chromatographed on silica gel (13 g) with elution proceeding as follows: 10% ethyl acetate/hexane (350 mL), nil; 20% ethyl acetate/hexane (50 mL), 0.012 g, recovered imine; (150 mL), nil; (250 mL), 0.048 g (24%) of 3-(2-chloro-pyridin-3-yl)-6-fluoro-2-[(2-flouro-phenylamino)-methyl]-3H-quinazolin-4-one as a white solid which had: mp 180–182° C.; $^1$H NMR δ 8.62 (d, J=5 Hz, 1 H), 7.95–7.91 (m, 2 H), 7.80 (d, J=8 Hz, 1 H), 7.57 (dt, J=3, 8 Hz, 1 H), 7.50 (dd, J=5, 8 Hz, 1 H), 7.01–6.91 (m, 2 H), 6.71 (dd, J=7, 12 Hz, 1 H), 6.53 (t, J=9 Hz, 1 H), 4.05 (ABq, $\Delta v_{1-3}$=19 Hz, J=17 Hz, 2 H); APCI MS m/z=399 (P+1).

EXAMPLE 15

3-(2-Chloro-phenyl)-6-fluoro-2-[(2-fluoro-phenylamino)-methyl]-3H-quinazolin-4-one A mixture of 3-(2-chloro-phenyl)-6-fluoro-3,4-dihydro-quinazolin-4-one-2-carboxaldehyde (0.10 g, 0.33 mmol), 2-fluoroaniline (0.064 mL, 0.66 mmol) and acetic acid (0.038 mL, 0.66 mmol) in methanol (10 mL) was stirred 1.5 hours at ambient temperature. Sodium cyanoborohydride (0.083 g, 1.32 mmol) was added and the reaction was stirred overnight. The reaction was diluted with water and concentrated to remove most of the methanol. The milky white liquid residue was treated with saturated aqueous bicarbonate and extracted with ethyl acetate. The organic layer was washed with aqueous bicarbonate and brine, dried over magnesium sulfate and concentrated. The residue was flash chromatographed on silica gel (20 g) eluting the product with 5% and then 10% ethyl acetate/hexane. In this fashion 0.10 g (76%) of 3-(2-chloro-phenyl)-6-fluoro-2-[(2-fluoro-phenylamino)-methyl]-3H-quinazolin-4-one was isolated as a yellow foam which had: $^1$H NMR δ 7.95 (dd, J=3, 8.5 Hz, 1 H), 7.85 (dd, J=5, 9 Hz, 1 H), 7.69 (dd, J=2, 7.5 Hz, 1 H), 7.63–7.46 (m, 3 H), 7.43–7.37 (m, 1 H), 7.05–6.90 (m, 2 H), 6.70–6.62 (m, 1 H), 6.43 (dt, J=1, 9 Hz, 1 H), 5.30 (br s, 1 H), 3.91 (ABq, $\Delta v_{1-3}$=27.5 Hz, J=17 Hz, 2 H). Analysis calculated for $C_{21}H_{14}ClF_2N_3O \cdot 0.25\ H_2O$: C, 62.70; H, 3.63; N, 10.44. Found: C, 62.78; H, 3.51; N, 10.29.

EXAMPLE 16

3-(2-Chloro-phenyl)-6-fluoro-2-[(6-methyl-pyridin-2-ylamino)-methyl]-3H-quinazolin-4-one A mixture of 3-(2-chloro-phenyl)-6-fluoro-3,4-dihydro-quinazolin-4-one-2-carboxaldehyde (0.170 g, 0.56 mmol) and 2-amino-6-picoline (0.050 g, 0.46 mmol), in methanol (10 mL) was refluxed overnight. The reaction was concentrated and the residue was flash chromatographed on silica gel (25 g). Elution proceeded as follows: 10% ethyl acetate/hexane (500 mL), nil; 20% ethyl acetate/hexane (300 mL), nil; (100 mL), 0.082 g of intermediate imine; (300 mL), 0.192 g of a mixture of starting material and imine. The pure imine (0.082 g 0.21 mmol) was dissolved in ethanol (10 mL) and 10% palladium on carbon (0.082 g) and formic acid (0.357 mL, 9.45 mmol) were added. The reaction was stirred at ambient temperature for 24 hours. The reaction was carefully neutralized with sodium bicarbonate and then filtered through celite. The pad was well washed with ethyl acetate. The filtrate was concentrated to afford 0.068 g (82%) of 3-(2-chloro-phenyl)-6-fluoro-2-[(6-methyl-pyridin-2-ylamino)-methyl]-3H-quinazolin-4-one as a colorless oil which had: $^1$H NMR δ 7.92 (dd, J=3, 8 Hz, 1 H), 7.80 (dd, J=5, 9 Hz, 1 H), 7.65–7.64 (m, 1 H), 7.53–7.48 (m, 4 H), 7.43–7.40 (m, 1 H), 7.37–7.31 (m, 1 H), 6.47 (d, J=7 Hz, 1 H), 6.25 (d, J=8 Hz, 1 H), 4.18 (dd, J=5, 18 Hz, 1 H), 4.00 (dd, J=5, 18 Hz, 1 H), 2.37 (s, 3 H); APCI MS m/z=395 (P+1).

EXAMPLE 17

3-(2-Chloro-phenyl)-2-[(2-fluoro-phenylamino)-methyl]-3H-thieno[3,2-d]pyrimidin-4-one A mixture of 3-(2-chloro-phenyl)-4-oxo-3,4-dihydro-thieno[3,2-d]pyrimidine-2-carbaldehyde (0.435 g, 1.5 mmol), 2-fluoroaniline (0.121 mL, 1.25 mmol), and anhydrous sodium sulfate (2.1 g 15 mmol) in glacial acetic acid (10 mL) was stirred overnight at ambient temperature. Sodium triacetoxyborohydride (0.795 g, 3.75 mmol) was added in one portion and the reaction was stirred for four hours. The reaction was carefully poured into saturated aqueous sodium bicarbonate and repeatedly extracted with methylene chloride. The combined organic phase was washed with water and brine, dried over sodium sulfate and concentrated. The residue was flash chromatographed on silica gel eluting with 2:1 hexane/ethyl acetate. After elution of a 50 mL forerun, 15 mL fractions were collected. Fractions 3–12 were combined and concentrated to afford 0.190 g (39%) of 3-(2-chloro-phenyl)-2-[(2-fluoro-phenylamino)-methyl]-3H-thieno[3,2-d]pyrimidin-4-one as a tan solid which had: mp 175–176° C.; $^1$H NMR δ 7.84 (d, J=5.5 Hz, 1 H), 7.66 (dd, J=1.5, 8 Hz, 1 h), 7.53 (sym m, 2 H), 7.42 (d, J=5.5 Hz, 1 H), 7.37 (dd, J=2, 7 Hz, 1 H), 6.97 (ddd, J=1.5, 8, 11.5 Hz, 1 H), 6.90 (t, J=7.5 Hz, 1 H), 6.63 (sym m, 1 H), 6.40 (dt, J=1.5, 9 Hz, 1 H), 5.17 (br s, 1 H), 3.96 (dd, J=5.5, 17 Hz, 1 H), 3.87 (dd, J=5, 17 Hz, 1 H). Analysis calculated for $C_{19}H_{13}ClFN_3OS$: C, 59.15; H, 3.40; N, 10.89. Found: C, 58.96; H, 3.41; N, 11.17.

EXAMPLE 18

3-(2-Chloro-phenyl)-2-[(3-pyrrolidin-1-ylmethyl-phenylamino)-methyl]-3H-thieno[3,2-d]pyrimidin-4-one Hydrochloride To a mixture of 3-(2-chloro-phenyl)-4-oxo-3,4-dihydro-thieno[3,2-d]pyrimidine-2-carbaldehyde (0.326 g, 1.13 mmol) and 3-(pyrrolidin-1-yl-methyl)-aniline (0.132 g, 0.75 mmol) in dichloroethane (10 mL) was added sodium triacetoxyborohydride (0.477 g, 2.25 mmol) portion wise. The reaction was stirred for 24 hours, and then carefully poured into saturated aqueous sodium bicarbonate and repeatedly extracted with chloroform. The combined organic phase was washed with water and brine, dried over magnesium sulfate and concentrated. The residue was flash chromatographed on silica gel (12 g, packed in chloroform). After eluting with chloroform (25 mL), elution was continued with 2–5% methanol/chloroform. Fractions containing the product [silica gel tlc $R_f$=0.20 (9:1 chloroform/methanol with 1% triethylamine)] were combined and concentrated to afford 0.166 g (53%) of the free base of the title product as a viscous oil which had: $^1$H NMR δ 7.84 (d, J=5.5 Hz, 1 H), 7.65 (m, 1 H), 7.52 (sym m, 2 H), 7.40 (d, J=5 Hz, 1 H), 7.37 (m, 1 H), 7.07 (t, J=8 Hz, 1 H), 6.66 (d, J=7.5 Hz, 1 H), 6.61 (s, 1 H), 6.37 (dd, J=2, 8 Hz, 1 H), 5.02 (br t, J=5 Hz, 1 H), 3.94 (dd, J=5, 17 Hz, 1 H), 3.84 (dd, J=5, 17 Hz, 1 H), 3.51 (s, 2 H), 2.48 (br s, 4 H), 1.75 (br s, 4 H). This oil was taken up in ether and treated with 1 N ethereal hydrochloric acid (0.75 mL, 0.75 mmol). The resulting slurry was concentrated and dried to afford 0.115 g (31%) of 3-(2-chloro-phenyl)-2-[(3-pyrrolidin-1-ylmethyl-phenylamino)-methyl]-3H-thieno[3,2-d]pyrimidin-4-one hydrochloride as a tan solid which had: mp 148–151° C.

EXAMPLE 19

3-(2-Chloro-phenyl)-6-fluoro-2-(2-fluoro-benzylamino)-3H-quinazolin-4-one

A suspension of 265 mg (0.87 mmol) of 3-(2-chloro-phenyl)-6-fluoro-2-thioxo-2,3-dihydro-1H-quinazolin-4-one in 2.0 mL of $POCl_3$ was treated with 300 mg of $PCl_5$ and the mixture was refluxed for 2.5 hours. The solvent was evaporated and the residues were taken up in ethyl acetate, washed with water and brine, and then the solvent was evaporated to give 2-chloro-3-(2-chloro-phenyl)-6-fluoro-3H-quinazolin-4-one as a solid. This material was dissolved in 10 mL of absolute ethanol and 216 mg ( 1.73 mmol) of 2-fluorobenzylamine and the mixture was refluxed overnight. The reaction mixture was cooled and the solvent was evaporated. The residues were partitioned between ethyl acetate and dilute HCl and the aqueous phase was extracted further with ethyl acetate. The combined organic extracts were dried with brine and with magnesium sulfate ($MgSO_4$)

EXAMPLE 20

3-(2-Chloro-phenyl)-6-fluoro-2-[(pyridin-2-ylmethyl)-amino]-3H-quinazolin-4-one

A suspension of 306 mg (1.0 mmol) of 3-(2-chloro-phenyl)-6-fluoro-2-thioxo-2,3-dihydro-1H-quinazolin-4-one in 2.0 mL of POCl$_3$ was treated with 350 mg of PCl$_5$ and the mixture was refluxed for 2.5 hours. The solvent was evaporated and the residues were taken up in ethyl acetate, washed with water and brine, and then the solvent was evaporated to give 2-chloro-3-(2-chloro-phenyl)-6-fluoro-3H-quinazolin-4-one as a solid. This material was dissolved in 15 mL of absolute ethanol and 238 mg (2.20 mmol) of 2-aminomethylpyridine and the mixture was refluxed overnight. The reaction mixture was cooled and the solvent was evaporated. The residue was dissolved in ethyl acetate and washed twice with water. The organic layer was dried with brine and with MgSO$_4$ and evaporated to give a gum which was crystallized from ether to give 190 mg (50%) of the desired product, m.p. 156–158° C.

Preparation 1

3-(2-Chloro-pyridin-3-yl)-6-fluoro-3,4-dihydro-quinazolin-4-one-2-carboxaldehyde A mixture of 3-(2chloro-pyridin-3-yl)-6-fluoro-2-methyl-3,4-dihydro-quinazolin-4-one (3.5 g, 12.0 mmol) and dimethylformamide dimethyl acetal (3.2 mL, 24 mmol) in dimethylformamide (12 mL) was refluxed for 24 hours. The reaction was cooled to ambient temperature and concentrated at reduced pressure to afford an orange solid. The solid was triturated with ethanol and the yellow crystalline solid was collected and dried to give 3.61 g (87%) of 3-(2-chloro-pyridin-3-yl)-6-fluoro-2-(2-dimethylamino-vinyl)-3,4-dihydro-quinazolin-4-one, which had: mp 197–200° C.; H $^1$H NMR δ 8.46 (dd, J=1.5, 5 Hz, 1 H), 7.85 (d, J=12.2 Hz, 1 H), 7.70 (dd, J=3, 8.5 Hz, 1 H), 7.68–7.65 (m, 1 H), 7.45–7.38 (m, 2 H), 7.31 (dt, J=3, 8.5 Hz, 1 H), 3.87 (d, J=12.2 Hz, 1 H), 2.80 (br s, 6 H). Analysis calculated for C$_{17}$H$_{14}$ClFN$_4$O: C, 59.22; H, 4.09; N, 16.25. Found: C, 59.14; H, 3.96; N, 16.25.

To a mixture of sodium periodate (1.9 g, 8.7 mmol) in tetrahydrofuran (10 mL) and aqueous pH 7 buffer (15 mL) was added 3-(2-chloro-pyridin-3-yl)-6-fluoro-2-(2-dimethylamino-vinyl)-3,4-dihydro-quinazolin-4-one (1.0 g, 2.90 mmol) all at once. The reaction was stirred for 1 hour. The precipitate was collected, washed well with water and dried under a nitrogen stream to afford 0.863 g (92%) of 3-(2-chloro-pyridin-3-yl)-6-fluoro-3,4-dihydro-quinazolin-4-one-2-carboxaldehyde as a yellow solid which was about a 25:1 mixture of hydrate to free aldehyde. The product was characterized as follows: mp 160–164° C.; $^1$H NMR (DMSO$_{d6}$) δ (hydrate) 8.51 (dd, J=2, 5 Hz, 1 H), 8.08 (dd, J=2, 8 Hz, 1 H), 7.87–7.78 (m, 3 H), 7.60 (dd, J=5, 8 Hz, 1 H), 6.64 [ABq, Dn$_{1-3}$=18 Hz, J=7 Hz, 2 H (hydrate OHs], 5.27 [br s, 1 H (hydrate methine CH]. Addition of D$_2$O to the NMR sample caused the multiplet at 6.64 ppm to disappear and sharpened up the singlet at 5.27 ppm. The presence of free aldehyde was demonstrated by a minor singlet at 9.51 ppm.

Preparation 2

3-(2-Chloro-phenyl)-6-fluoro-3,4-dihydro-quinazolin-4-one-2-carboxaldehyde

A mixture of 3-(2-chloro-phenyl)-6-fluoro-2-methyl-3,4-dihydro-quinazolin-4-one (1.0 g, 3.46 mmol) and dimethylformamide dimethyl acetal (0.92 mL, 6.92 mmol) in dimethylformamide (4 mL) was heated to 140° C. for 24 hours. The reaction was cooled to ambient temperature and concentrated at reduced pressure. The dark residue was triturated with methanol and the bright yellow crystalline solid which formed was collected and dried to give 1.075 g (90%) of 3-(2-chloro-phenyl)-6-fluoro-2-(2-dimethylamino-vinyl)-3,4-dihydro-quinazolin-4-one which had: mp 210–211° C.; $^1$H NMR δ 7.86 (d, J=12.3 Hz, 1 H), 7.79 (dd, J=3, 8.5 Hz, 1 H), 7.61–7.54 (m, 1 H), 7.51–7.29 (m, 5 H), 4.06 (d, J=12.3 Hz, 1 H), 2.80 (br s, 6 H). Analysis calculated for C$_{18}$H$_{15}$ClFN$_3$O: C, 62.89; H, 4.40; N, 12.22. Found: C, 62.75; H, 4.28; N, 12.29.

To a well stirred mixture of sodium periodate (2.24 g, 10.47 mmol) in pH 7 buffer (10 mL) and tetrahydrofuran (10 mL) was added 3-(2-chloro-phenyl)-6-fluoro-2-(2-dimethylamino-vinyl)-3,4-dihydro-quinazolin-4-one (0.90 g, 2.62 mmol) all at once. The mixture warmed slightly to the touch and was stirred 1 h at ambient temperature. The reaction was filtered through celite and the pad was rinsed with ethyl acetate. The phases were separated from the filtrate and the aqueous layer was extracted with ethyl acetate. The combined organic phase was washed with brine, dried over magnesium sulfate, and concentrated to afford 0.802 g (97%) of 3-(2-chloro-phenyl)-6-fluoro-3,4-dihydro-quinazolin-4-one-2-carboxaldehyde as a 1:2 mixture of free aldehyde and hydrate which had: $^1$H NMR δ 9.52 (s,) [CHO], 8.20–7.45 (m, 7 H), 6.75 (d, J=7.4 Hz) [hydrate OH] and 6.49 (d, J=8 Hz) [hydrate OH], 5.14 (t, J=7.5 Hz) [hydrate methine CH].

Preparation 3

6-Fluoro-3,4-dihydro-3-(2-methyl-pyridin-3-yl)-quinazolin-4-one-2-carboxaldehyde A mixture of 6-fluoro-3,4-dihydro-2-methyl-3-(2-methyl-pyridin-3-yl)-quinazolin-4-one (1.02 g, 3.79 mmol) and dimethylformamide dimethyl acetal (1.01 mL, 7.58 mmol) in dimethylformamide (5 mL) was heated to 140° C. for 24 hours. Additional dimethylformamide dimethyl acetal (2 mL) was added and the reaction was heated at 140° C. for 16 hours. The reaction was cooled to ambient temperature and concentrated at reduced pressure. The dark residue was triturated with ether and the dark purple crystalline solid which formed was collected and dried to give 0.69 g (56%) of 6-fluoro-2-(2-dimethylamino-vinyl)-3,4-dihydro-3-(2-methyl-pyridin-3-yl)-quinazolin-4-one which had: $^1$H NMR δ 8.61 (dd, J=1.5, 5 Hz, 1 H), 7.87 (d, J=12.3 Hz, 1 H), 7.78 (dd, J=3, 8.5 Hz, 1 H), 7.50–7.45 (m, 2 H), 7.39–7.29 (m, 2 H), 3.97 (d, J=12.3 Hz, 1 H), 2.86 (br s, 6 H), 2.35 (s, 3 H).

To a well stirred mixture of sodium periodate (1.76 g, 8.26 mmol) in pH 7 buffer (10 mL) and tetrahydrofuran (15 mL) was added 6-fluoro-2-(2-dimethylamino-vinyl)-3,4-dihydro-3-(2-methyl-pyridin-3-yl)-quinazolin-4-one (0.69 g, 2.12 mmol) all at once. The mixture warmed slightly to the touch and was stirred for 1 hour at ambient temperature. The reaction was concentrated at reduced pressure and the residue treated with a 1:2 mixture of water and chloroform. The tan solid was collected, washed well with water and chloroform and dried under a stream of nitrogen to afford 0.50 g (80%) of 6-fluoro-3,4-dihydro-3-(2-methyl-pyridin-3-yl)-quinazolin-4-one-2-carboxaldehyde as a 1:1 mixture of free aldehyde and hydrate which had: mp 175–177° C.; $^1$H NMR δ 9.46 (s, 0.5 H) [CHO], 8.53 (br s, 1 H), 8.10–8.07 (s, 0.5 H), 7.94–7.70 (m, 3.5 H), 7.39–7.32 (m, 1 H), 6.59 (br s, 0.5 H) [hydrate OH], 6.47 (br s, 0.5 H) [hydrate OH], 5.17 (s, 0.5 H) [hydrate methine CH], 2.20 (s, 3 H); APCI MS m/z=284.1 (P+1).

Preparation 4

3-(2-Chloro-phenyl)-4-oxo-3,4-dihydro-thieno[3,2-d]pyrimidine-2-carbaldehyde A mixture of 3-(2-chloro-phenyl)-2-methyl-4-oxo-3,4-dihydro-thieno[3,2-d]pyrimidine (9.4 g, 34.06 mmol) and dimethylformamide dimethyl acetal (9.0, 68.12 mmol) in dimethylformamide (70 mL) was heated to 140° C. for 24 hours. The reaction was cooled to ambient temperature and concentrated at reduced pressure (50° C. bath temperature). The residue was slurried in methanol and concentrated at reduced pressure. This methanol slurry/concentration procedure was repeated twice. The residue was triturated with methanol and the light yellow crystalline solid which formed was collected and dried to give 10.1 g (85%) of 3-(2-chloro-phenyl)-2-(dimethylamino-vinyl)-4-oxo-3,4-dihydro-thieno[3,2-d]pyrimidine which had: $^1$H NMR δ 7.83 (d, J=12.5 Hz, 1 H), 7.68 (d, J=5 Hz, 1 H), 7.57 (m, 1 H), 7.41 (m, 2 H), 7.31 (m, 1 H), 7.14 (d, J=5 Hz, 1 H), 4.06 (d, J=12.5 Hz, 1 H), 2.77 (br s, 6 H).

To a well stirred mixture of sodium periodate (9.7 g, 45.3 mmol) in pH 7 buffer (115 mL) and tetrahydrofuran (115 mL) was added 3-(2-chloro-phenyl)-2-(dimethylamino-vinyl)-4-oxo-3,4-dihydro-thieno[3,2-d]pyrimidine (5.0 g, 15.1 mmol) all at once. The mixture warmed slightly to the touch and was stirred for 1 hour at ambient temperature. The reaction was filtered through celite and the pad was washed with ethyl acetate. The phases were separated from the filtrate and the aqueous layer was extracted with ethyl acetate. The combined organic phase was washed with brine, dried over sodium sulfate and concentrated to a yellow oil. The oil was flash chromatographed on silica gel (70 g) with elution proceeding as follows: 50% methylene chloride/hexane (500 mL), unweighed forerun; 50% ethyl acetate/hexane (1000 mL), 4.6 g (100%) of 3-(2-chloro-phenyl)-4-oxo-3,4-dihydro-thieno[3,2-d]pyrimidine-2-carboxaldehyde as a foam which was a 2:1 mixture of free aldehyde and hydrate and had: $^1$H NMR δ 9.56 (s) [CHO], 7.94 and 7.87 (pair of d, J=5.2, 5.4 Hz, respectively, 1 H), 7.60–7.30 (m, 5 H), 5.30 (dd, J=7, 9.5 Hz) [hydrate methine CH), 4.76 (d, J=9.5 Hz) [hydrate OH], 3.79 (d, J=7 Hz) [hydrate OH]. Note that the doublets at 4.76 and 3.79 ppm are washed out and the dd at 5.30 ppm is converted to a singlet when deuterium oxide is added to the NMR sample.

Preparation 5

3-(2-Chloro-phenyl)-3,4-dihydro-quinazolin-4-one-2-carboxaldehyde (A) A mixture of 3-(2-chloro-phenyl)-2-methyl-3,4-dihydro-quinazolin-4-one (1.0 g, 3.69 mmol) and dimethylformamide dimethyl acetal (0.64 mL, 4.8 mmol) in dimethylformamide (4 mL) was heated to 140° C. for 24 hours. Additional dimethylformamide dimethyl acetal (0.32 mL, 2.4 mmol) was added and heating was continued for an additional 24 hours. The reaction was cooled to ambient temperature and concentrated at reduced pressure (60° C. bath temperature). The dark residue was triturated with methanol and the pale orange solid which formed was collected and dried to give 0.75 g (62%) of 3-(2-chloro-phenyl)-2-(2-dimethylamino-vinyl)-3,4-dihydro-quinazolin-4-one which had: mp 228–230° C.; $^1$H $^1$H NMR δ 8.19 (d, J=8 Hz, 1 H), 7.91 (d, J=12.3 Hz, 1 H), 7.71–7.18 (m, 7 H), 4.10 (d, J=12.3 Hz, 1 H), 2.81 (br s, 6 H). Analysis calculated for $C_{18}H_{16}ClN_3O$: C, 66.36; H, 4.95; N, 12.90. Found: C, 66.20; H, 5.03; N, 12.79.

(B) To a well stirred mixture of sodium periodate (1.38 g, 6.45 mmol) in water (6 mL) and tetrahydrofuran (6 mL) was added 3-(2-chloro-phenyl)-2-(2-dimethylamino-vinyl)-3,4-dihydro-quinazolin-4-one (0.70 g, 2.15 mmol) all at once. The mixture warmed slightly to the touch and was stirred for 1 hour at ambient temperature. The reaction was filtered through celite and the pad was rinsed with ether. The filtrate was rendered basic by addition of saturated aqueous sodium bicarbonate and phases were separated. The aqueous layer was extracted with ethyl acetate. The combined organic phase was washed with brine, dried over potassium carbonate, and concentrated. The residue was flash chromatographed on silica gel (1×3 inches) with elution proceeding as follows: 50% methylene chloride/hexane (400 mL), nil; (100 mL) and 50% ethyl acetate/hexane (150 mL), 0.51 g (82%) of 3-(2-chloro-phenyl)-3,4-dihydro-quinazolin-4-one-2-carboxaldehyde as about a 1:1 mixture of free aldehyde and hydrate which contained about 20% of 3-(2-chloro-phenyl)-3,4-dihydro-quinazolin-4-one-2-carboxaldehyde (from simple hydrolysis of the enamine; exists exclusively in its enolized form to take advantage of an internal hydrogen bond to N1 of the quinazolin-4-one). Identifying features of each of the components of this mixture can be observed in the NMR spectrum as defined in the table below:

TABLE

Key NMR shifts of the components in preparation 5 (ppm)

| 2-carboxaldehyde | Hydrated 2-carboxaldehyde | Enolized 2-Acetaldehyde |
| --- | --- | --- |
| 9.60 (s) [CHO] | 5.30 (m) [methine CH] <br> 4.94 (d, J = 9.3 Hz) [OH] <br> 3.90 (d, J = 7.2 Hz) [OH] | 8.71 (d, J = 3.7 Hz) and 4.40 (d, J = 3.7 Hz) [enol protons, cis coupled] |

Consistent with preparations 1–4, execution of preparation 5 in pH 7 buffered water will suppress formation of the enolized 2-acetaldehyde side product.

Preparation 6

3-(2-Chloro-phenyl)-6-fluoro-2-thioxo-2,3-dihydro-1H-quinazolin-4-one

A solution of 1.04 g (6.71 mmol) of 5-fluoroanthranilic acid and 1.13 g (6.71 mmol) of 2-chlorophenylisothiocyanate in 10 ml of glacial acetic acid was refluxed for 2.5 hours. The reaction mixture was cooled and the acetic acid was evaporated to give a yellow solid residue, which was taken up in ethyl acetate and ether. The solid was filtered off and washed with ether and air dried to give 1.48 g (72%) of the desired product, m.p. 295–297° C.

Separation of Atropisomers by HPLC

EXAMPLE 21

The HPLC separation of the atropisomers of 3-(2-Chloro-phenyl)-6-fluoro-2-[(3-pyrrolidin-1-ylmethyl-phenylamino)-methyl]-3H-quinazolin-4-one is described below.

| Column | Chiralpak AD |
| --- | --- |
| Mobile Phase | 85/15 hexane/isopropyl alcohol with 0.1% diethylamine |
| Flow Rate | 1 mL/min |

-continued

| Column | Chiralpak AD |
|---|---|
| Detection | UV (250 nM) |
| Retention Time (first atropisomer) | 13.635 min |
| Retention Time (second atropisomer) | 16.509 min |

EXAMPLE 22

The HPLC separation of the atropisomers of 2-{[3-(2-Chloro-pyridin-3-yl)-6-fluoro-4-oxo-3,4-dihydro-quinazolin-2-ylmethyl]-amino}-benzonitrile is described below.

| Column | Chiralpak AD |
|---|---|
| Mobile Phase | 70/30 hexane/isopropyl alcohol with 0.1% diethylamine |
| Flow Rate | 1 mL/min |
| Detection | UV (335 nM) |
| Retention Time (first atropisomer) | 8.522 min |
| Retention Time (second atropisomer) | 14.101 min |

What is claimed is:
1. A compound of the formula

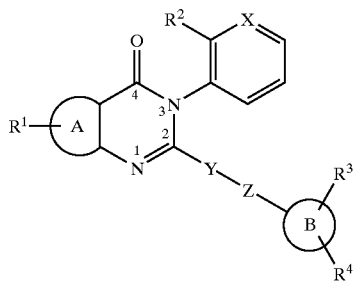

I wherein A is a thieno fused aromatic ring;
B is phenyl, pyridyl or pyrimidyl;
X is N or CH;
Y and Z represents —CH$_2$NH— or —NHCH$_2$—;
R$^1$ is selected from hydrogen, (C$_1$–C$_6$)alkyl optionally substituted with from one to three fluorine atoms, cyano, halo, amino, nitro and (C$_1$–C$_6$)alkoxy optionally substituted with from one to three fluorine atoms;
R$^2$ is halo, cyano, (C$_1$–C$_6$)alkyl optionally substituted with from one to three fluorine atoms, nitro, amino, (C$_1$–C$_6$)alkylthio, (C$_1$–C$_6$)alkoxy optionally substituted with from one to three fluorine atoms, hydroxyl, H—C(=O)—, (C$_1$–C$_6$)alkyl—O—C(=O)— or NH$_2$—C(=O)—;
R$^3$ and R$^4$ are selected, independently, from hydrogen, (C$_1$–C$_6$)alkyl optionally substituted with from one to three fluorine atoms, halo, cyano, hydroxy (C$_1$–C$_6$) alkoxy optionally substituted with from one to three fluorine atoms, —C(=O)H, —CH$_2$—OR$^5$ and —CH$_2$NR$^6$R$^7$;
R$^5$ is hydrogen, (C$_1$–C$_6$)alkyl or —C(=O)(C$_1$–C$_6$)alkyl; and
R$^6$ and R$^7$ are selected, independently, from hydrogen, (C$_1$–C$_6$)alkyl and —C(=O)(C$_1$–C$_6$)alkyl; or
R$^6$ and R$^7$, taken together with the nitrogen to which they are attached, form a four to seven membered saturated or unsaturated ring wherein one of the carbon atoms of such ring may optionally be replaced by oxygen or nitrogen; or a pharmaceutically acceptable salt of such compound.

2. A compound according to claim 1 wherein R$^2$ is halo, methyl or trifluoromethyl.

3. A compound according to claim 1 wherein R$^1$ and R$^2$ are both halo.

4. A compound according to claim 1 wherein R$^3$ is selected from hydrogen, methyl, cyano, fluoro, formyl and hydroxymethyl.

5. A compound according to claim 1 wherein R$^3$ is selected from hydrogen, methyl, cyano, fluoro, formyl and hydroxymethyl.

6. A compound according to claim 1 wherein R$^2$ is halo, methyl or trifluoromethyl.

7. A compound according to claim 1 wherein R$^3$ is 2-CH$_2$NR$^6$R$^7$, 3-CH$_2$NR$^6$R$^7$ or 6-CH$_2$NR$^6$R$^7$, wherein the NR$^6$R$^7$ moiety is a morpholine, piperidine o pyrrolidine ring.

8. A compound according to claim 1 wherein Y-Z is —CH$_2$NH—, and R$^1$ is fluoro.

9. A compound according to claim 1 wherein R$^2$ is halo, methyl or trifluoromethyl.

10. A compound according to claim 1 wherein Y-Z is —CH$_2$NH—, ring B is 2-pyridyl or phenyl and R$^3$ and R$^4$ are selected, independently, from cyano, fluoro, methyl, formyl, hydrogen and hydroxymethyl.

11. A compound according to claim 1 wherein said compound is selected from the group consisting of:

3-(2-chlorophenyl)-2-[(2-fluoro-phenylamino)-methyl]-3H-thieno[3,2-d]pyrimidin-4-one; and 3-(2-chloro-phenyl)-2-[(3-pyrrolidin-1-ylmethyl-phenylamino)-methyl]-3H-thieno[3,2-d]pyrimidin-4-one;

and the pharmaceutically acceptable salts of these compounds.

12. A pharmaceutical composition for treating a condition selected from migraine headaches and convulsions, subsequent to cardiac bypass surgery and grafting, in a mammal, comprising an amount of a compound according to claim 1 that is effective in treating such condition and a pharmaceutically acceptable carrier.

13. A pharmaceutical composition for treating a condition selected from migraine headaches and convulsions, subsequent to cardiac bypass surgery and grafting, in a mammal, comprising an AMPA receptor antagonizing effective amount of a compound according to claim 1 and a pharmaceutically acceptable carrier.

14. A method for treating a condition selected from migraine headaches and convulsions, subsequent to cardiac bypass surgery and grafting, in a mammal, comprising administering to a mammal requiring such treatment an amount of a compound according to claim 1 that is effective in treating such condition.

15. A method for treating a condition selected from migraine headaches and convulsions, subsequent to cardiac bypass surgery and grafting, in a mammal, comprising administering to a mammal requiring such treatment an AMPA receptor antagonizing effective amount of a compound according to claim 1.

* * * * *